United States Patent
Nedilko et al.

(10) Patent No.: US 9,031,791 B2
(45) Date of Patent: May 12, 2015

(54) SYSTEM AND METHOD FOR DETECTING ROCK FALL

(75) Inventors: Bohdan Nedilko, Burnaby (CA); Iain Weir-Jones, Vancouver (CA)

(73) Assignee: Weir-Jones Engineering Consultants Ltd., Vancouver, British Columbia (CA)

( * ) Notice: Subject to any disclaimer, the term of this patent is extended or adjusted under 35 U.S.C. 154(b) by 1111 days.

(21) Appl. No.: 12/972,334

(22) Filed: Dec. 17, 2010

(65) Prior Publication Data

US 2011/0313671 A1    Dec. 22, 2011

Related U.S. Application Data

(63) Continuation-in-part of application No. PCT/CA2009/000837, filed on Jun. 17, 2009.

(60) Provisional application No. 61/073,358, filed on Jun. 17, 2008.

(51) Int. Cl.
  *G01V 1/28*    (2006.01)
  *B61K 9/08*    (2006.01)
  *B61L 23/04*    (2006.01)

(52) U.S. Cl.
  CPC ........ *B61K 9/08* (2013.01); *B61L 23/041* (2013.01)

(58) Field of Classification Search
  USPC ............ 702/2, 14, 33, 39, 44, 48, 54, 56, 57, 702/60, 64, 75, 76, 176, 188, 189
  See application file for complete search history.

(56) References Cited

U.S. PATENT DOCUMENTS

| | | | |
|---|---|---|---|
| 889,205 A | 6/1908 | Cook | |
| 2,429,056 A | 10/1947 | Grosjean | |
| 3,794,977 A | 2/1974 | Thorne-Booth et al. | |
| 5,001,682 A * | 3/1991 | Anderson | 367/186 |
| 5,713,540 A | 2/1998 | Gerszberg et al. | |
| 6,185,153 B1 * | 2/2001 | Hynes et al. | 367/124 |
| 6,216,985 B1 * | 4/2001 | Stephens | 246/120 |
| 7,510,531 B2 * | 3/2009 | Lee et al. | 600/534 |
| 7,578,794 B2 * | 8/2009 | Hatlestad et al. | 600/508 |
| 2005/0251343 A1 * | 11/2005 | Zehavi | 702/18 |
| 2006/0257066 A1 | 11/2006 | Hill et al. | |

FOREIGN PATENT DOCUMENTS

| | | |
|---|---|---|
| CN | 1187439 | 7/1998 |
| CN | 101066679 | 11/2007 |
| JP | 2000180219 | 6/2000 |
| JP | 2001307290 | 11/2001 |
| JP | 200517230 | 1/2005 |
| KR | 20020005241 | 1/2002 |
| WO | 2010055293 | 5/2010 |

OTHER PUBLICATIONS

Tsuji et al., JP 11-256503 (English-machine translated; as best as understood).*

* cited by examiner

*Primary Examiner* — Hyun Park
(74) *Attorney, Agent, or Firm* — Todd Rattray; Oyen Wiggs Green & Mutala LLP

(57) ABSTRACT

Aspects of the invention provide systems and methods for using ballast sensors to detect rock fall events in a vicinity of railway tracks or similar roadways or tracks. The ballast sensors are spaced apart from the tracks. Particular embodiments permit the use of signals from the ballast sensors to discriminate rock fall events from other types of events and to detect the hypocenter of a rock fall event.

64 Claims, 18 Drawing Sheets

SYSTEM AND METHOD FOR DETECTING ROCK FALL

RELATED APPLICATIONS

This application is a continuation in part of Patent Cooperation Treaty application No. PCT/CA2009/000837 filed 17 Jun. 2009, published under WO2010/003220 and entitled SYSTEM AND METHOD FOR DETECTING ROCK FALL. This application also claims the benefit of the priority of U.S. application No. 61/073,358 filed on 17 Jun. 2008 and entitled SEISMIC ROCK FALL DETECTION SYSTEM.

TECHNICAL FIELD

This invention relates to detection of rock fall events. Particular embodiments provide systems and methods for rock fall detection.

BACKGROUND

Rock fall events and other similar events (e.g. avalanches and washouts) which take place in a vicinity of railway tracks can damage the track, can damage passing trains and, in some cases, can derail passing trains which can in turn cause significant damage to the train and to people and/or property being transported by the train. Damaged trains can cause corresponding damage to the environment. Similar events which take place in a vicinity of other transport-ways (e.g. roadways, bridges, subway tracks and the like) can cause similar damage.

Prior art technology for detecting rock fall in a vicinity of railway tracks involves so called "slide fences." Slide fences incorporate current carrying wires which extend between fence posts alongside the railway track. Falling rock may strike and break one or more of these wires, opening the corresponding circuits and preventing current flow therethrough. This change of current flow may be detected to generate a rock fall indicator. Slide fences are unreliable, because falling rock may not strike or break a wire, but may still represent a danger to a passing train. Slide fences also tend to generate false positive results, for example, when the wire are broken by animals or the like. Additionally, if a slide fence triggers (i.e. a wire is broken), then the slide fence must be repaired (i.e. the broken wire must be replaced) and rail traffic may be delayed until the slide fence is repaired.

There is a general desire for systems and methods of rock fall detection that overcome or ameliorate these and/or other deficiencies with the prior art.

SUMMARY OF THE INVENTION

One aspect of the invention provides a system for detection of rock fall in a vicinity of a section of railway track. The system comprises: a plurality of ballast sensors spaced apart along the track section, each ballast sensor located in a ballast proximate to the track section but spaced apart from rails and ties associated with the track section and each ballast sensor sensitive to acoustic energy and configured to generate a corresponding ballast sensor signal in response to detecting acoustic energy; and a signal processing unit operatively connected to receive the ballast sensor signals from the plurality of ballast sensors, the signal processing unit configured to detect rock fall events in a vicinity of the track section based, at least in part, on the ballast sensor signals.

Another aspect of the invention provides a method for detection of rock fall in a vicinity of a section of railway track. The method involves: providing a plurality of ballast sensors spaced apart along the track section and locating each ballast sensor in a ballast proximate to the track section but spaced apart from rails and ties associated with the track section, each ballast sensor sensitive to acoustic energy and configured to generate a corresponding ballast sensor signal in response to detecting acoustic energy; receiving the ballast sensor signals from the plurality of ballast sensors; and processing the ballast sensor signals to detect rock fall events in a vicinity of the track section based, at least in part, on the ballast sensor signals.

Other aspects of the invention provide computer program products comprising computer instructions which, when executed by a processor, cause the processor to carry out the methods of the invention.

Other features and aspects of specific embodiments of the invention are described below.

BRIEF DESCRIPTION OF THE DRAWINGS

In drawings which depict non-limiting embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Aspects of the invention provide systems and methods for using ballast sensors to detect rock fall events in a vicinity of railway tracks or similar tracks. The ballast sensors are spaced apart from the tracks. Particular embodiments permit the use of signals from the ballast sensors to discriminate rock fall events from other types of events and to detect the hypocenter of a rock fall event.

Figure 1:
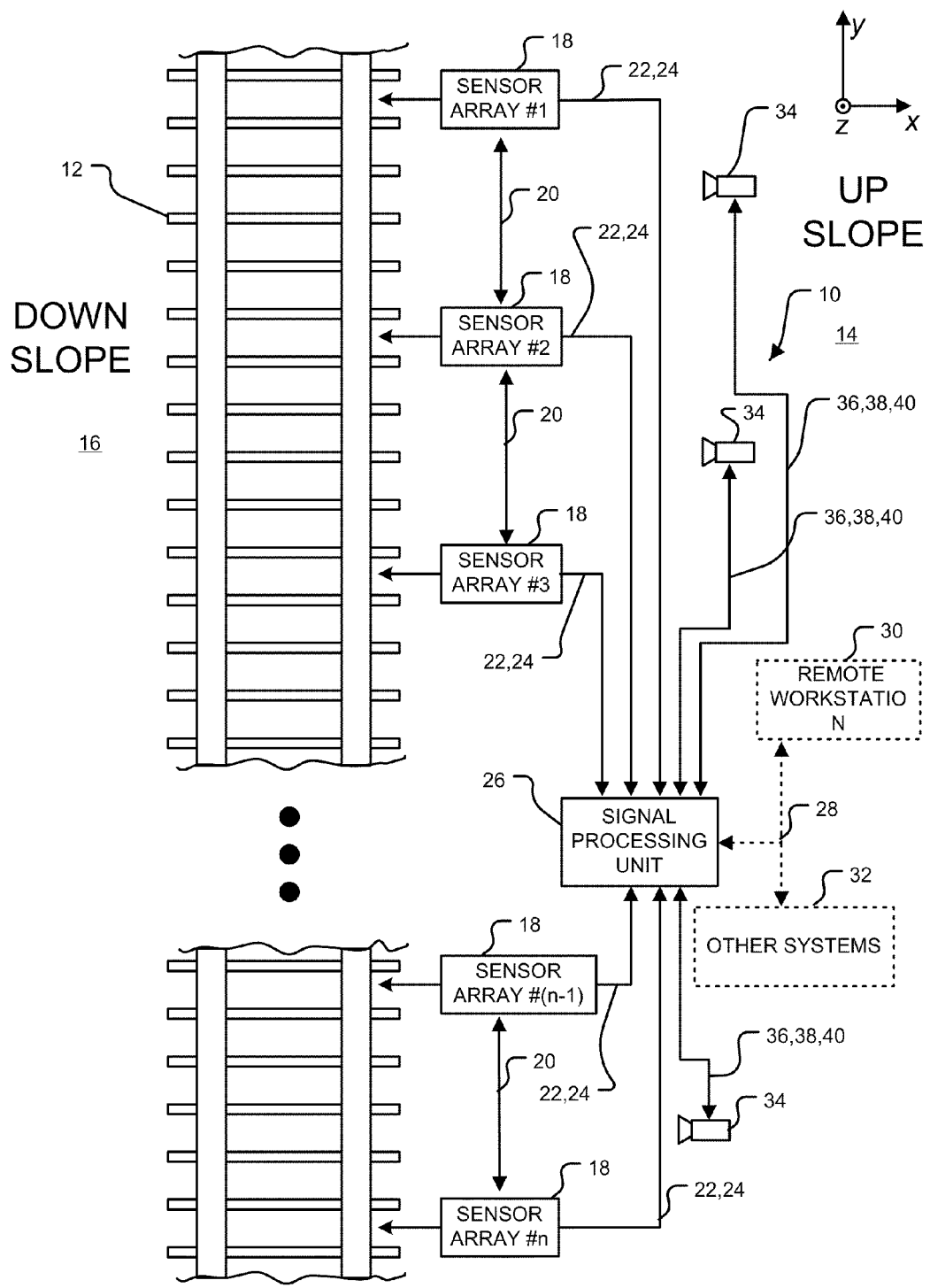
FIG. 1 is a schematic depiction of a rock fall detection system according to a particular embodiment configured to detect rock fall in a vicinity of a section of railway track.

FIG. 1 is a schematic depiction of a rock fall detection system 10 according to a particular embodiment configured to detect rock fall in a vicinity of a section of railway track 12. Track section 12 may typically be located in a sloped region which may present a risk of rock fall from the up slope 14 toward the downslope 16. This is not necessary. Track section 12 may be located in a valley and may have upward slopes on both sides thereof. In some embodiments, the length of track section 12 may be in a range of 100 m-5 km. In other embodiments, track section 12 may have other lengths. To facilitate this description, a number of direction conventions are used. As shown by the schematic axes shown in FIG. 1, the z direction refers to the vertical direction (i.e. the direction of gravity), the y direction is oriented along track section 12 and the x direction refers to the direction that crosses track section 12.

Rock fall system 10 comprises a plurality of sensor arrays 18 disposed along track section 12. As discussed in more detail below, sensor arrays 18 comprise one or more sensors for detecting acoustic and/or vibrational energy. In the illustrated embodiment, there are n sensor arrays 18 corresponding to track section 12. In general, the number n may be any suitable number that provides the functionality described below and may depend on the geotechnical characteristics of the substrate in a vicinity of track section 12.

Sensor arrays 18 are spaced apart from one another by distances 20 in y-direction. In some embodiments, distances 20 are in a range of 5-100 m. In other embodiments, this range is 10-50 m. In still other embodiments, this range is 10-30 m. Distances 20 may be based on a number of factors, including, by way of non-limiting example: characteristics of sensors used in sensor arrays 18 (e.g. types of sensors, signal to noise ratio, etc.), geotechnical characteristics (e.g. quality factor of geologic substrate), performance requirements (e.g. magnitude of rock fall which it is desired for system 10 to detect) and/or other factors (e.g. local weather patterns, local natural and/or man-made sources of noise). Distances 20 may be uniform within system 10, but this is not necessary. In general, distances 20 may differ between each adjacent pair of sensor arrays 18.

Each of sensor arrays 18 generates one or more corresponding sensor signals 22. In the illustrated embodiment sensor signals 22 are analog signals, but this is not necessary. In some embodiments, sensor arrays 18 may output digital sensor signals. Sensor signals 22 are transmitted along transmission lines 24 to central signal processing unit 26. Transmission lines, 24 may run through protective conduits (not shown in FIG. 1), such as pipes made of suitable metals, plastics, fiber or the like. Transmission lines 24 may be electrically shielded to prevent electrical interference from external sources and/or to prevent cross-talk between signals 22. The schematic illustration of FIG. 1 shows a single signal 22 and a single transmission line 24 for each sensor array 18. This is not necessary. In general, sensor arrays 18 may comprise multiple sensors that generate a corresponding plurality of signals 22 which in turn may be transmitted to signal processing unit 26 on a corresponding plurality of transmission lines 24. It will be appreciated by those skilled in the art that signals 22 from sensor arrays 18 may be multiplexed on transmission lines 24 if desired.

In the illustrated embodiment, system 10 comprises one or more optional image capturing devices 34. Image capturing devices 34 may comprise closed circuit television cameras, for example. In some embodiments, image capturing devices 34 capture digital images and/or digital video. Image capturing devices 34 may be controlled by signal processing unit 26 using signals 38 which are delivered to image capturing devices along transmission lines 40. Image data 36 captured by image capturing devices 34 may be transmitted to signal processing unit 26 along the same transmission lines 40. Transmission lines 40 may represent more than one actual line. In some embodiments, transmission lines 40 are not required and camera control signals 38 may be wirelessly transmitted from signal processor unit 26 to image capturing devices 34 and image data 36 may be wirelessly transmitted from image capturing devices 34 back to signal processing unit 26.

Signal processing unit 26 may be housed in a suitably protective enclosure (not shown)—e.g. a small building or the like. At signal processing unit 26, sensor signals 22 are digitized and processed to detect rock fall events. Processing signals 22 to detect rock fall events, which is described in more detail below, may involve discriminating rock fall events from other events. By way of non-limiting example, such other events may include passing trains, passing highrail vehicles (e.g. trucks that travel on track section 12), other natural noise sources (e.g. waterfalls, falling trees or animals) and/or other man-made noise sources (e.g. power generators or pedestrians).

System 10 may optionally include a network connection 28 to a remote workstation 30. Network connection 28 may be a wire network connection, a wireless network connection and/or a fiber optic network connection, for example. In some embodiments, remote workstation 30 may be connected to system 10 via network connection 28 to perform a number of functions, which may include (by way of non-limiting example): monitoring the status of system 10, logging or storing data captured by system 10, recalibrating or reconfiguring system 10, updating software used by system 10 or the like. In some embodiments, some or all of the data captured by sensor arrays 18 may be transmitted via network connection 28 to remote workstation 30 and such data may be processed at the remote workstation 30 to detect rock fall events in a similar manner that rock fall events are detected by signal processing unit 26, as described in more detail below.

System 10 may be a modular part of a greater system (not shown) which incorporates other systems 32 similar to system 10. For example, signal processing unit 26 may be optionally linked (via network connection 28 or via some other network connection) to similar signal processing units for other systems 32 similar to system 10.

In the illustrated embodiment of FIG. 1, sensor arrays 18 are located on uphill side 14 of track section 12. This is not necessary. In some embodiments, sensor arrays 18 may be additionally or alternatively located on downhill side 16 of track section 12. In some embodiments, a single sensor array 18 may comprise a plurality of acoustic or vibrational energy sensors, some of which may be located on uphill side 14 and some of which may be located on downhill side 16.

Sensor arrays 18 may each comprise one or more acoustic energy sensors. By way of non-limiting example, suitable acoustic energy sensors may include: electromagnetic induction based sensors (which may be referred to as geophones), accelerometers, piezoelectric sensors, electroactive polymer based sensors, optical sensors, capacitive sensors, micromachined sensors or the like. As is known in the art, some acoustic energy sensors may be directional—e.g. some acoustic sensors may have one or more axes on which they are more sensitive to acoustic energy. In some embodiments, the output of these acoustic energy sensors may be generally correlated with (e.g. proportional to) the sensed acoustic energy. In other embodiments, the output of these acoustic energy sensors may be generally correlated with (e.g. proportional to) other parameters, such as displacement, velocity or acceleration of a sensor component.

Figure 2A:
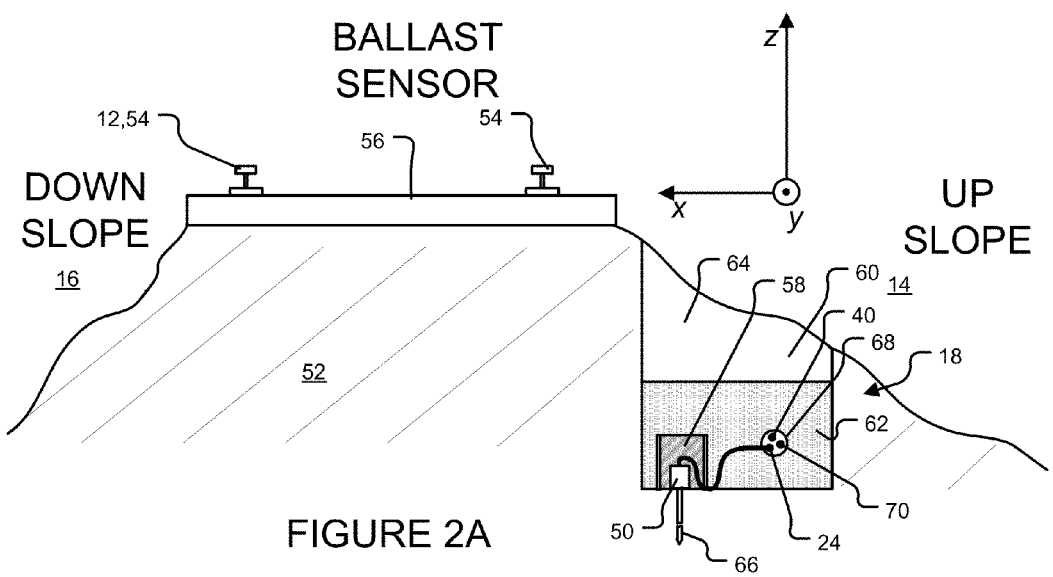
FIG. 2A shows a sensor array according to a particular embodiment which is suitable for use with the FIG. 1 rock fall detection system and which incorporates a ballast sensor.

FIG. 2A illustrates a sensor array 18 according to a particular embodiment which is suitable for use with rock fall detection system 10. In the FIG. 2A embodiment, sensor array 18 comprises a single, uni-axial, electromagnetic induction-type sensor 50 which is located on uphill side 14 of track section 12. Sensor 50 is located in the ballast 52 which supports track section 12 and is spaced apart from track section 12—i.e. sensor 50 is not in direct contact with tracks 54 or ties 56. In this description, this type of sensor 50 (which is located at least in part in ballast 52 of track section 12 and is spaced apart from track section 12) may be referred to as a ballast sensor. Sensor 50 may be encased in a protective housing 58, which (in the illustrated embodiment) comprises a grout-filled enclosure which may be made from a suitable material such as suitable plastic, fiber, steel or the like.

Protective housing 58 (and sensor 50) may be located in a trench 60 which is excavated in ballast 52 alongside track section 12. In the illustrated embodiment, a region 62 surrounding housing 58 is filled with compacted sand, which may improve acoustic conduction and/or protect sensor 50 and transmission line 24 from sharp rocks which may be present in ballast 52, and a remaining region 64 of trench 60 is back-filled with ballast 52. In the illustrated embodiment sensor 50 is coupled to an anchoring stake 66 which may be driven into the substrate below ballast 52 and/or below sand-filled region 62. Stake 66 may be situated, shaped and/or otherwise configured to provide good acoustic coupling to the geologic substrate in a region of track section 12.

As mentioned above, sensor 50 of the FIG. 2A embodiment is a uni-axial sensor. The sensitivity axis of sensor 50 is the z axis and sensor 50 generates a single corresponding signal 22. In one particular embodiment, signal 22 is generally correlated with (e.g. proportional to) a sensed velocity of a component of sensor 50. However, as discussed above, in other embodiments, signal 22 may be generally correlated with (e.g. proportional to) other parameters, such sensed displacement, acceleration or energy of corresponding sensor components. The inventors have determined that uni-axial (z axis) sensors are sufficient for the purposes of detecting rock fall on suitably steep slopes. It will be appreciated that uni-axial sensors are less costly than multi-axial sensors. In some environments or in some applications, however, it may be desirable to incorporate multi-axial sensors. Accordingly, in some embodiments, sensor 50 may be multi-axial or sensor array 18 may comprise a plurality of uni-axial sensors oriented in different directions. In such embodiments, the number of signals 22 generated by a multi-axial sensor may correspond to its number of axes or the number of signals 22 generated by a plurality of uni-axial sensors may correspond to the number of uni-axial sensors.

As discussed above, sensor 50 is electronically connected to transmission line 24 for transmission of a corresponding sensor signal 22 to signal processing unit 26. As shown in FIG. 2A, transmission line 24 may run through a suitable protective conduit 68, which may be made from a suitable material such as suitable plastic, fiber, steel or the like. In some embodiments, conduit 68 may also house cables 70 (e.g. electrical and/or optical cables) which form part of network connection 28 between system 10 and remote workstation 30 and/or other systems 32 (see FIG. 1) and/or transmission lines 40 associated with optional image capturing devices 34.

Figure 2B:
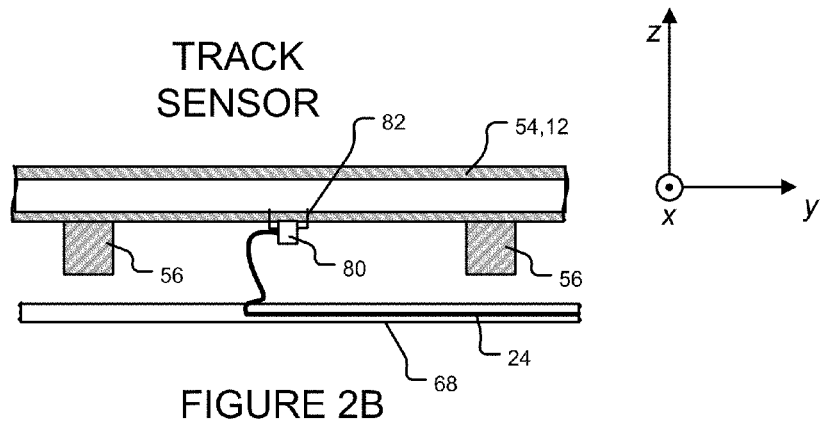
FIG. 2B shows a rail sensor which may be incorporated into any one or more of sensor arrays of the FIG. 1 rock fall detection system.

FIG. 2B illustrates a sensor 80 which may be incorporated into any one or more of sensor arrays 18. In FIG. 2B embodiment, sensor 80 is similar in many respects to sensor 50 (FIG. 2A) in that sensor 80 is a uni-axial, electromagnetic induction-type sensor. Sensor 80 differs from sensor 50 in that sensor 80 is mounted (via suitable mounting hardware 82) to track 54 as opposed to being a ballast sensor which is spaced apart from track 54. Sensors which are mounted to track section 12 (including track(s) 54 and/or ties 56) may be referred to in this description as rail sensors. In other respects, sensor 80 may be similar to sensor 50 described above.

Experiments have determined that rail sensors may be more sensitive to direct contact between falling rocks and track section 12 (e.g. track(s) 54 and/or ties 56) and may be more sensitive to passing trains or highrail vehicles. In some embodiments, therefore, it is desirable to include one or more rail sensors. However, in some embodiments, it is desirable to include ballast sensors rather than rail sensors or only ballast sensors, because: ballast sensors may be less prone to damage by trains passing along track section 12, ballast sensors may be more robust to maintenance of track section 12 which may involve physical manipulation of track section 12 (e.g. lifting track section 12 away from ballast 52), ballast sensors may produce more uniform signals, ballast sensors may exhibit greater differences in spatial attenuation and may therefore lead to more accurate location of the hypocenter of rock fall events and ballast sensors may be less sensitive to high frequency vibrations which may permit lower sampling rates and correspondingly higher bit resolution for the same data acquisition hardware.

Figure 3:
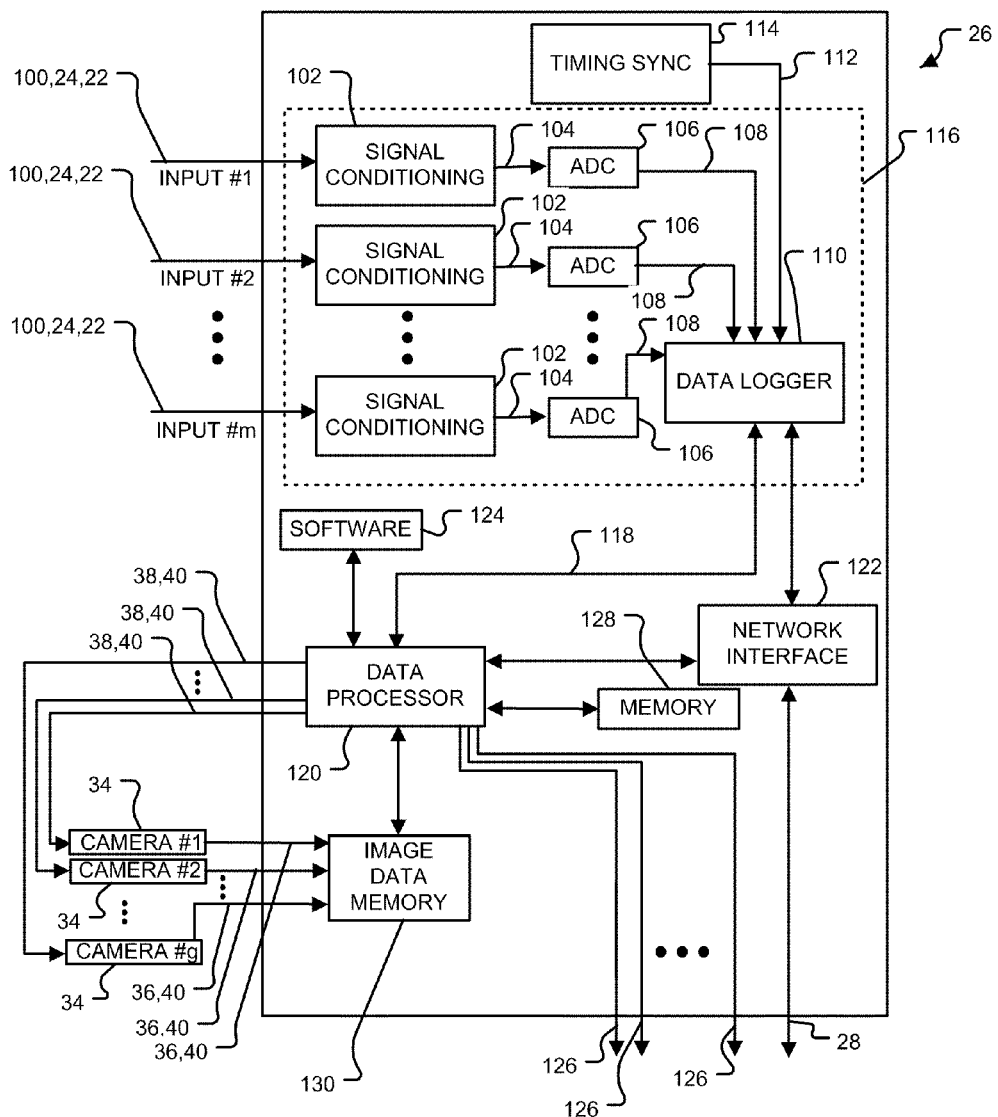
FIG. 3 is a schematic illustration of a signal processing unit according to a particular embodiment which is suitable for use with the FIG. 1 rock fall detection system.

FIG. 3 is a schematic illustration of a signal processing unit 26 according to a particular embodiment which is suitable for use with rock fall detection system 10. In the illustrated embodiment, signal processing unit 26 comprises a plurality m of inputs 100 corresponding to transmission lines 24 and signals 22 from sensor arrays 18. Each input signal 100 is provided to corresponding signal conditioning circuitry 102. Suitable signal conditioning circuitry 102 is well known to those skilled in the art and, by way of non-limiting example, may comprise anti-aliasing filter(s) and amplifier(s). Conditioned sensor signals 104 are then provided to analog-to-digital converters (ADCs) 106. ADCs 106 sample conditioned sensor signals 104 and provide corresponding digital sensor signals 108. In one particular embodiment, ADCs 106 provide 24 bits of digital resolution (i.e. digital sensor signals 108 comprise a sequence of 24 bit samples), but this is not necessary. In other embodiments, ADCs 106 may output digital sensor signals 108 having other suitable bit depths. The sampling rate of ADCs 106 may be selected to be sufficiently fast to accommodate the frequencies of interest, as described in more detail below.

Digital sensor signals 108 output from ADCs 106 are provided to data logger 110. In addition to receiving digital sensor signals 108, data logger 110 also receives timing synchronization signal 112 from timing synchronization source 114. In one particular embodiment, timing synchronization source 114 comprises a global positioning satellite (GPS) receiver which receives timing information from one or more satellite sources. A GPS-based timing synchronization source 114 is particularly useful in embodiments, where system 10 is a modular component system of a larger system that includes other component system(s) 32 (FIG. 1), which other component systems 32 may have their own signal processing units 26 and their own timing synchronization sources 114. In such systems, GPS-based timing synchronization sources 114 could provide synchronous timing signals 112 across modular component system 10 and other component systems 32. In other embodiments, where there is only one signal processing unit 26, timing synchronization source 114 may comprise one or more other sources of timing information. By way of non-limiting example, timing synchronization source 114 may access timing information from an internal or external quartz piezo-electric oscillator, timing synchronization source 114 may comprise a real time clock or a suitable hardware timing chip or the like.

Using timing synchronization signal 112 and digital sensors signals 108, data logger 110 time stamps, collects and logs the data generated by sensor arrays 118 (FIG. 1). Data logger 110 may have access to memory (not expressly shown) and may use any suitable data structure(s) or database protocol(s) for logging digital sensor signals 108 and corresponding time stamp information from synchronization signal 112. Data logger 110 may store information in a manner that is indexed, or otherwise accessible, by time stamp indicia, by corresponding sensor, and/or by occurrence of an event (as explained in more detail below). In some embodiments, data logger 110 may be operatively connected (via network interface 122 and network connection 28) to remote workstation 30 and/or to other systems 32 (see FIG. 1). Processor 120 and/or data logger 110 may perform data compression to save local storage space and/or network bandwidth. In the illustrated embodiment, data logger 110 is also operatively connected (via interface 118) to embedded data processor 120.

In some embodiments, signal conditioning circuitry 102, ADCs 106, and/or data logger 110 may be implemented by a data acquisition unit (DAU) 116. Various DAUs are known to those skilled in the art and are commercially available from a number of sources. In some embodiments, DAU 116 may also incorporate its own timing synchronization source 114. In some embodiments, DAU 116 may include other components which are not expressly shown in the FIG. 3 illustration. By way of non-limiting example, such components may include digital processing components (e.g. digital filters) or the like. Suitable DAUs include, by way of non-limiting example, the TMA-24 Microseismic Acquisition Unit available from Terrascience Systems Ltd. of Vancouver, Canada and other suitable DAUs. In some embodiments, it is desirable that the DAU sample at a rate greater than or equal to 500 Hz with a bid resolution of 16 or more bits.

Commercially available DAUs 116 may have a limited number of inputs 100 or a limited data storage capacity. In some embodiments, therefore, signal processing unit 26 may comprise a plurality of DAUs 16, each of which may be configured in a manner similar to that described herein.

Data logger 110 is operatively connected (via interface 118) to data processor 120. Data processor 120 may be part of a suitably configured computer system (not shown) or may be part of an embedded system. Processor 120 shown schematically in FIG. 3 may comprise more than one individual data processor which may be centrally located and/or distributed. Processor 120 may comprise internal memory (not shown) and/or have access to external memory 128. Processor 120 may be programmed with, or otherwise have access to, software 124. As explained in more detail below, processor 120 may execute software 124 which may in turn cause processor 120 to process data obtained from data logger 110 and to generate one or more outputs 126. Processor 120 may also control the operation of DAU 116, data logger 110 and/or system 10 via interface 118. In some embodiments, processor 120 may be operatively connected (via network interface 122 and network connection 28) to remote workstation 30 and/or to other systems 32 (see FIG. 1). Processor 120 may output some or all of outputs 126 to remote workstation 30 and/or to other systems 32 via network interface 122 and network connection 28.

In embodiments where system 10 includes optional image capturing devices 34, signal processing unit 26 may also comprise image data memory 130 for storing image data 36 captured by image capturing devices 34. Image data 36 may be delivered to image data memory 130 along transmission lines 40 as shown in the illustrated embodiment or may be wirelessly delivered to image data memory 130 using a wireless transceiver (not shown). Data processor 120 may also control image capturing devices 34 using camera control signals 38 which may be transmitted to image capturing devices 34 along transmission lines 40 and/or wirelessly. Camera control signals 38 may permit image capturing devices 34 to move (e.g. pan), zoom, focus or the like and may control when and how image capturing devices 34 capture image data 36.

Figure 4A:
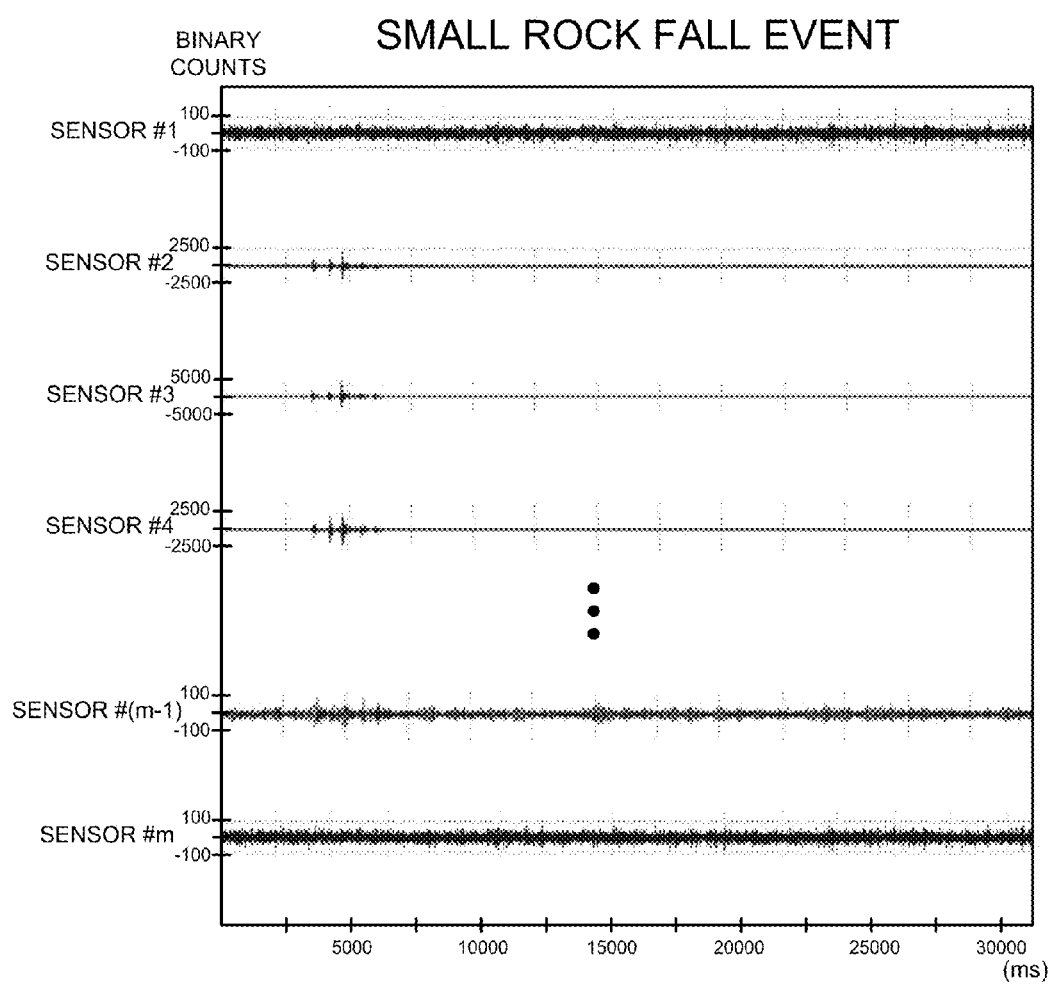
FIG. 4A is a plot showing digitized and time stamped sensor data typical for a small rock fall event obtained at the FIG. 3 data processor for a number of sensors.

FIG. 4A is a plot showing digitized and time stamped sensor data obtained at processor 120 for a number of sensors (e.g. sensors 50) within sensor arrays 18. The vertical axis of the FIG. 4A plot is measured in binary counts (e.g. digital values output by ADCs 106 and stored in data logger 110) and the horizontal axis of the FIG. 4A plot is measured in milliseconds (ms). As discussed above, acoustic energy sensors within sensor arrays 18 may output signals 22 that are generally correlated with sensed velocity of a sensor element. In such embodiments, the binary counts on the vertical axis of the FIG. 4A plot may also be correlated with this velocity. Where the acoustic energy sensors within sensor arrays 18 represent other parameters (e.g. displacement, acceleration, energy), the binary counts on the vertical axis of the FIG. 4A plot may be correlated with such other parameters. It should be noted that the scales of the vertical axis for the individual sensor plots within FIG. 4A are different for each sensor—i.e. the plots corresponding to sensors #1, #(m−1) and #m have ranges of approximately (−100,100) binary counts, the plots corresponding to sensors #2 and #4 have ranges of approximately (−2500,2500) and the plot corresponding to sensor #3 has a range of approximately (−5000,5000).

FIG. 4A shows typical digitized and time-stamped sensor data obtained at processor 120 for a small event that is detected in a region of sensors #2, #3 and #4 at a time around 3,000-7,000 ms. It can be seen that, in the 3,000-7,000 ms time period, the magnitude of the sensed signals of sensors #2, #3 and #4 (on the order of thousands of binary counts) is significantly greater than the background noise (on the order of hundreds of binary counts). This event is typical of a small scale rock fall, but may also be typical of other small scale events, such as (by way of non-limiting example): raveling of a rock face, a surge in adjacent waterfall activity, one or more animals, vegetation or fencing shaken by wind or the like. For typical applications alongside railways tracks, the scale of the FIG. 4A event may be interpreted to be sufficiently small that it is not of significant concern.

Figure 4B:
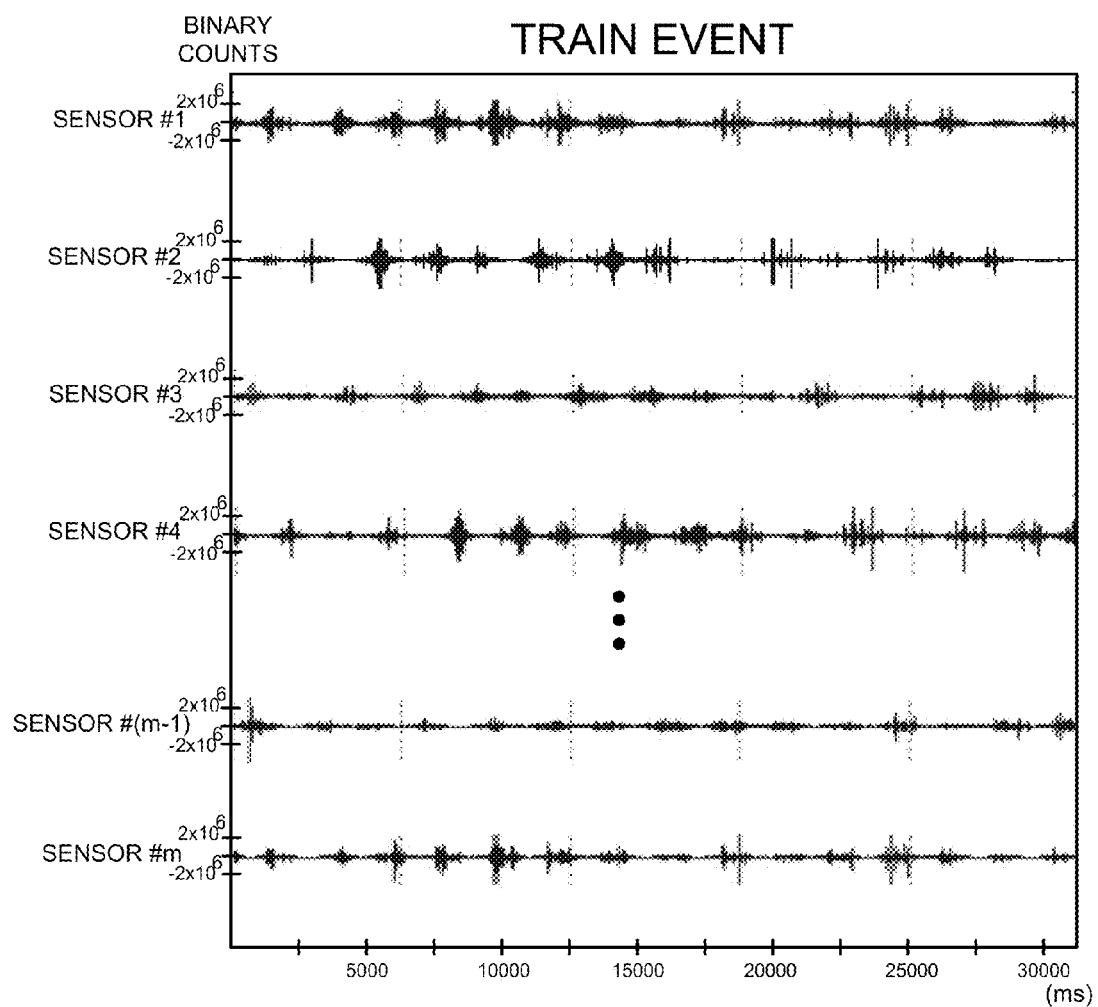
FIG. 4B is a plot showing digitized and time-stamped sensor data typical for a passing train obtained at the FIG. 3 data processor for a number of sensors.

FIG. 4B shows typical digitized and time-stamped sensor data obtained at processor 120 for a passing train. Like FIG. 4A, the vertical axis of the FIG. 4B plot is measured in binary counts and the horizontal axis is measured in milliseconds. However in the FIG. 4B plot, the vertical axes for each sensor are on the same scale ($-2\times10^6$, $2\times10^6$). It can be seen that the duration of the train event is significantly longer than the event of FIG. 4A.

Figure 4C:
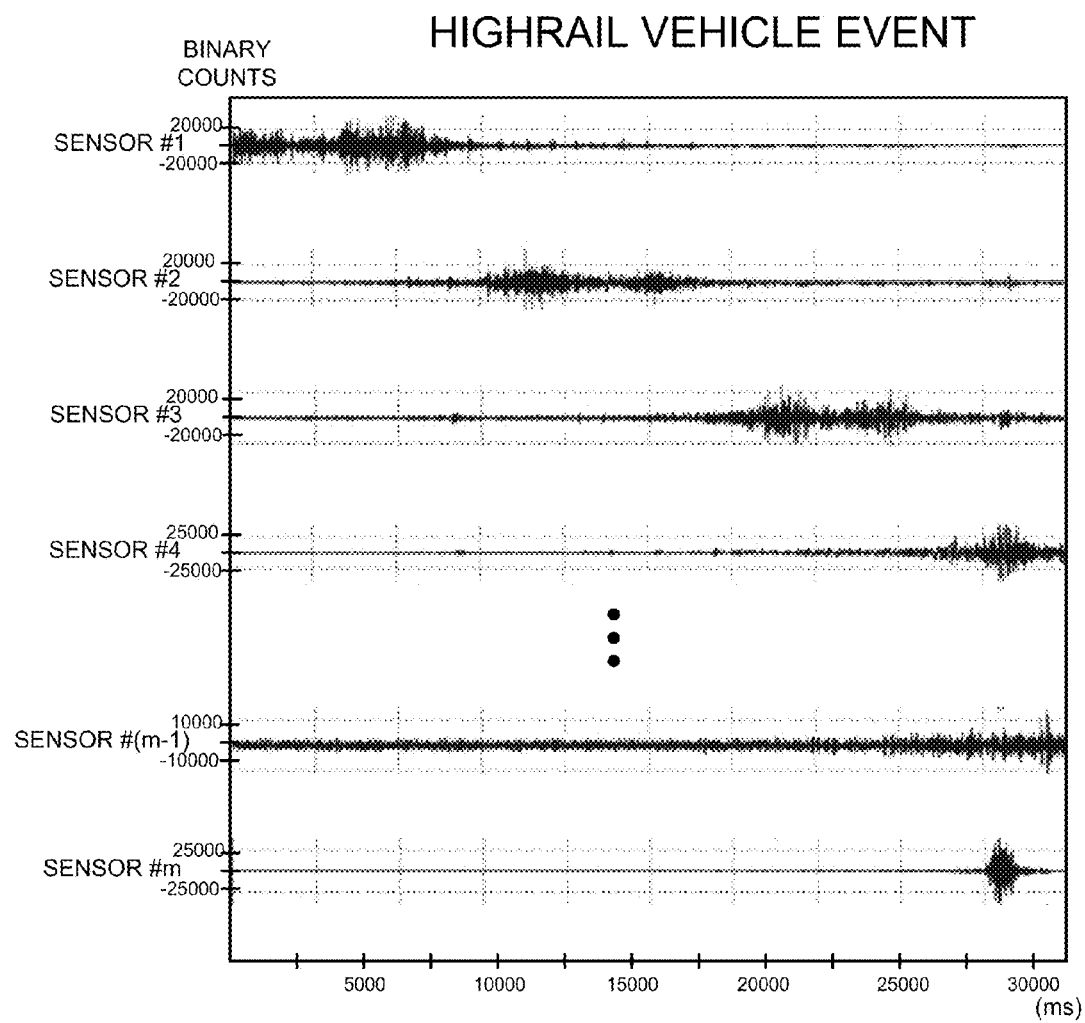
FIG. 4C is a plot showing digitized and time-stamped sensor data typical for a passing highrail vehicle obtained at the FIG. 3 data processor for a number of sensors.

FIG. 4C shows typical digitized and time-stamped sensor data obtained at processor 120 for a passing highrail vehicle. The vertical axis of the FIG. 4C plot is measured in binary counts and the horizontal axis is measured in milliseconds. While the vertical scales vary between the individual FIG. 4C plots for the individual sensors, it can be seen that the scales of the individual FIG. 4C plots for the highrail vehicle have scales that are lower than those of FIG. 4B for the train.

Figure 4D:
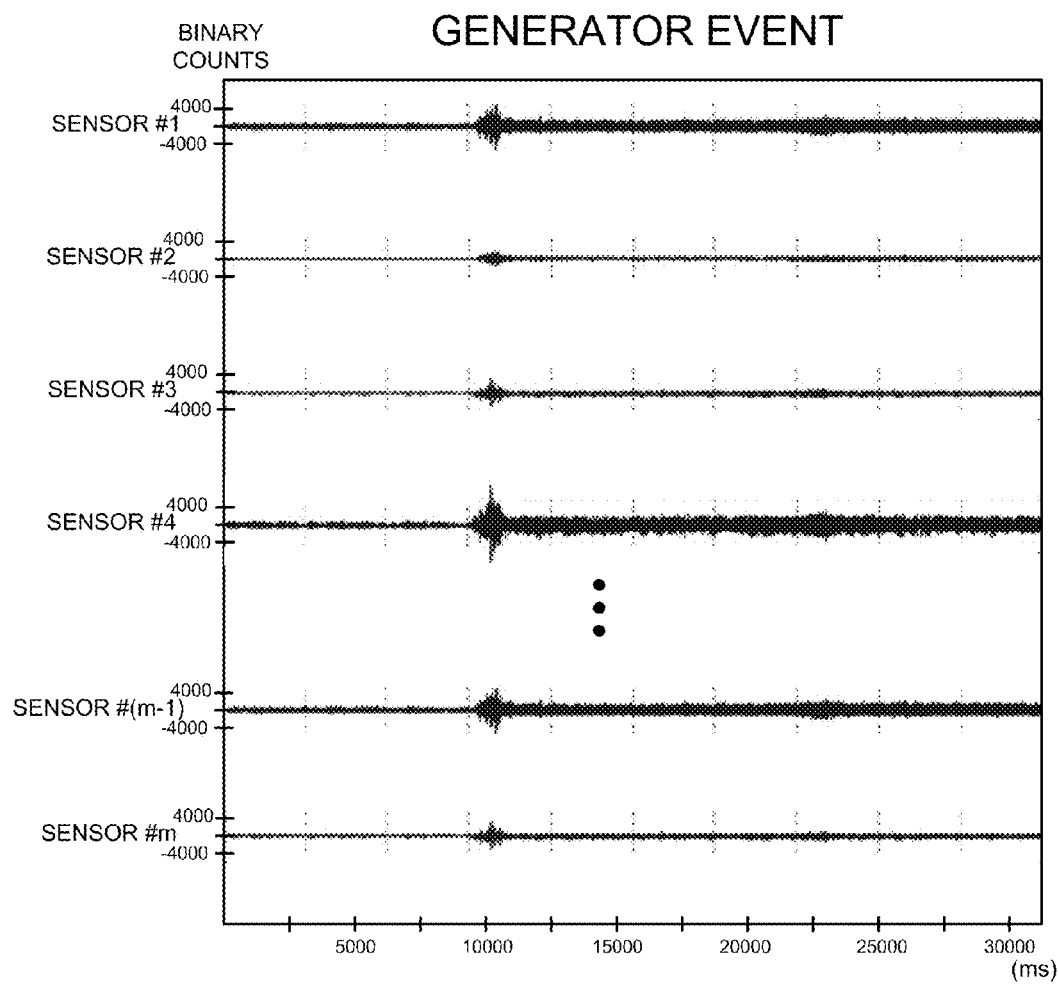
FIG. 4D is a plot showing digitized and time-stamped sensor data typical for the activation of an on-sited power generator obtained at the FIG. 3 data processor for a number of sensors.

In some environments, there may be additional sources of events which may be particular of the environment in which system 10 is deployed. One example of a such an event is the activation of a power generator in a vicinity of system 10. Where it is desired for system 10 to operate at a remote location, such a generator may be used to power system 10 itself. Such a generator is not required however and other sources of power (e.g. batteries, solar power or wind power) may be used to power system 10. FIG. 4D shows typical digitized and time-stamped sensor data obtained at processor 120 for the activation of a power generator in the vicinity of system 10. The vertical axis of the FIG. 4D plot is measured in binary counts and the horizontal axis is measured in milliseconds. The vertical axes for each sensor in the FIG. 4D plots is on the same scale (−4000,4000).

Figure 4E:
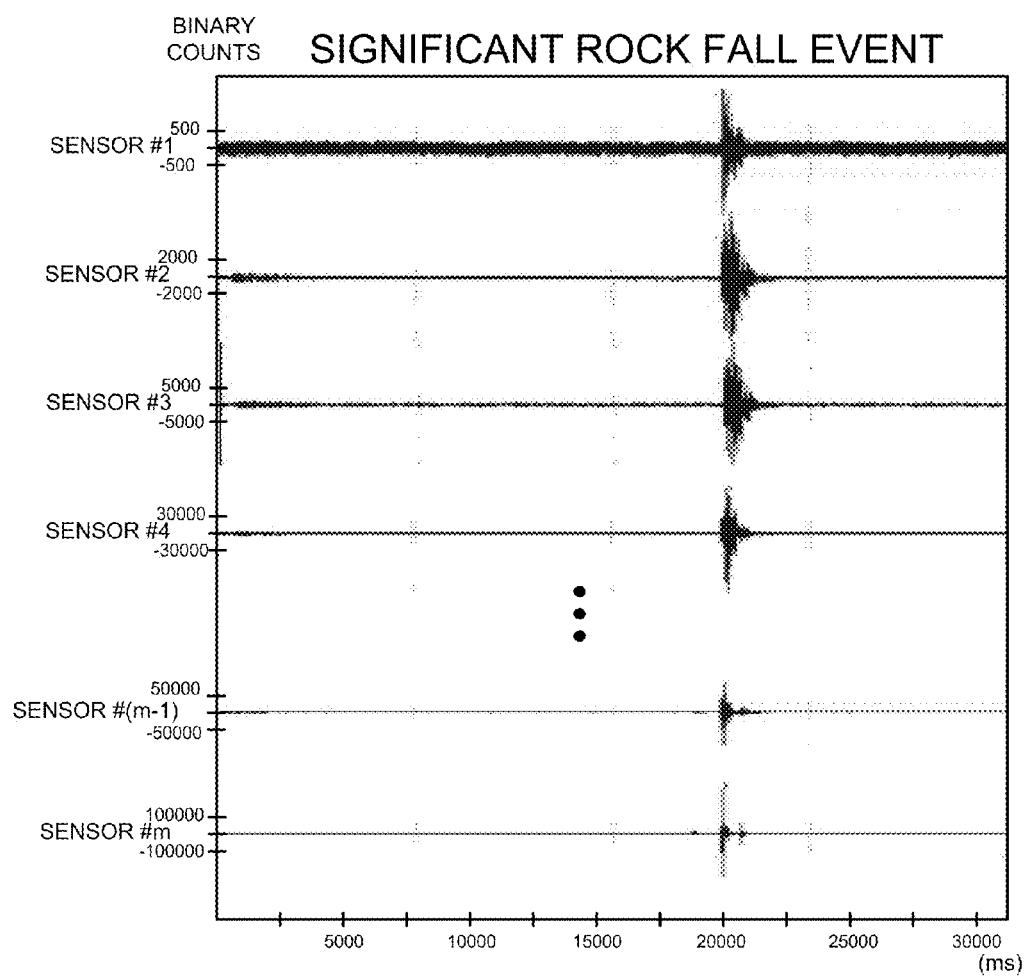
FIG. 4E is a plot showing digitized and time-stamped sensor data typical for a significant rock fall event obtained at the FIG. 3 data processor for a number of sensors.

FIG. 4E shows typical digitized and time-stamped sensor data obtained at processor 120 for a rock fall event that is of sufficient size to be of concern for typical railway applications. The vertical axis of the FIG. 4E plot is measured in binary counts and the horizontal axis is measured in milliseconds. It will be noted that the vertical scales vary between the individual FIG. 4E plots for the individual sensors. FIG. 4E indicates that the rock fall event took place between approximately 19,000-21,000 ms. Comparing the vertical scales of the various sensors and the corresponding magnitudes of the sensed signals, it would appear that the rock fall event occurred relatively closer to sensor #m than to any of the other illustrated sensors. Comparing the vertical scales and the corresponding magnitudes of the sensed signals between the FIG. 4E rock fall event and the FIG. 4A small scale event, it can be seen that the FIG. 4E rock fall event has significantly greater magnitude.

In some embodiments, rock fall detection by system 10 may be performed by signal processing unit 26 based on signals 22 received from sensor arrays 18 (see FIG. 1). In particular embodiments, rock fall detection by system 10 may involve processor 120 processing data from data logger 110 (or DAU 116) to detect rock fall events (see FIG. 3). In other embodiments, rock fall detection may be performed at remote workstation 30 and/or at other systems 32 having access to data from data logger 110 (or DAU 116) via network connection 28. For the remainder of this description, it is assumed, without loss of generality, that rock fall detection is performed by embedded processor 120 processing data received from data logger 110.

A part of rock fall detection performed by system 10 involves discriminating between rock fall events and other types of events which may be of less concern and/or between significant rock fall events and relatively small rock fall events which may be of less concern. An event that is determined by system 10 to be a significant rock fall event, but which in fact is a different event (e.g. a moving train, a train that has come to a stop in a vicinity of track section 12, a moving highrail vehicle, a highrail vehicle that has come to a stop in a vicinity of track section 12 (e.g. to perform maintenance on track section 12), an animal in a vicinity of track section 12 and/or a power generator) or is an insignificant rock fall event may be referred to in this description as a false positive detection result. In general, there is a desire to minimize false positive detection results.

Figure 5:
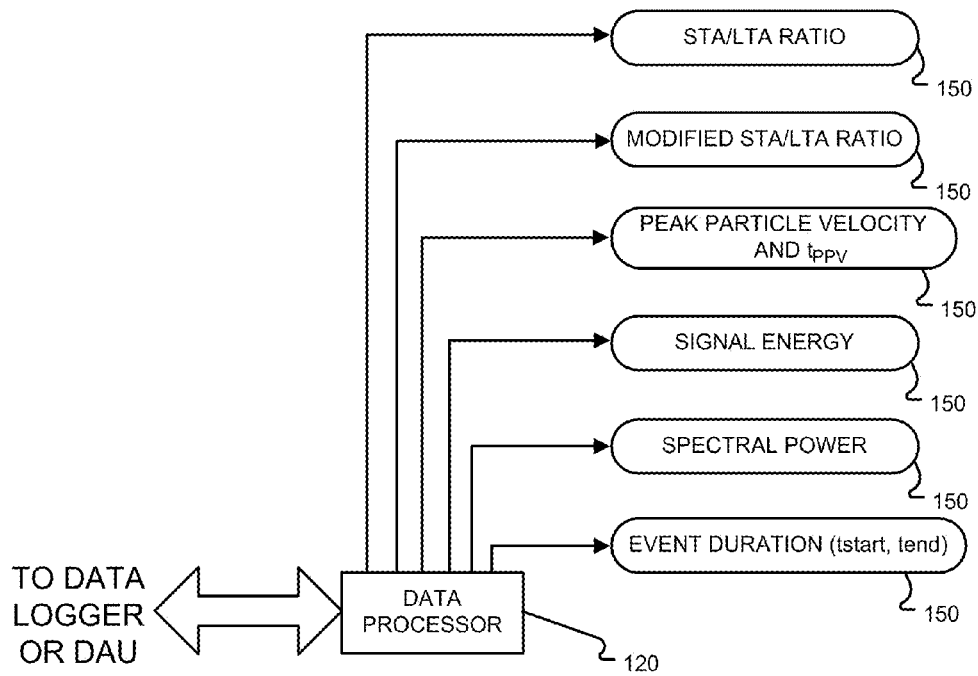
FIG. 5 schematically illustrates a number of processing parameters which may be determined from the sensor data.

To detect rock fall events while minimizing false positive detection results, processor 120 may process data received from data logger 110 to determine a plurality of processing parameters. Some or all of these processing parameters may be used in turn to discriminate rock fall events from other events. FIG. 5 schematically illustrates a number of processing parameters 150 which may be determined by processor 120 using data accessed from data logger 110. Each of these processing parameters 150 is explained in more detail below. In some embodiments, processor 120 may output one or more of processing parameters 150 as outputs 126. As discussed above, some or all of outputs 126 may be available to remote workstation 30 and/or other systems 32 via network connection 28.

Processor 120 may process the data corresponding to one or more sensors to determine a ratio of a short term average (STA) to a long term average (LTA), which may be one of the processing parameters 150. This ratio may be referred to as an STA/LTA average and may be computed according to:

$$\left(\frac{STA}{LTA}\right)_n = \frac{\sum_{i=(n-(a-1))}^{i=n} |x_i|}{\sum_{i=(n-(b-1))}^{i=n} |x_i|} \text{ where } b > a > 0 \text{ and } n \geq a, b \quad (1)$$

where: $x_i$ represents the value of the $i^{th}$ sample, n is the index of the current sample $x_n$, a is the STA duration (number of samples) and b is the LTA duration (number of samples). Examining equation (1), it will be appreciated that the STA and LTA durations a and b may be expressed as numbers of samples or equivalently as temporal durations.

Figures 6A, 6B:
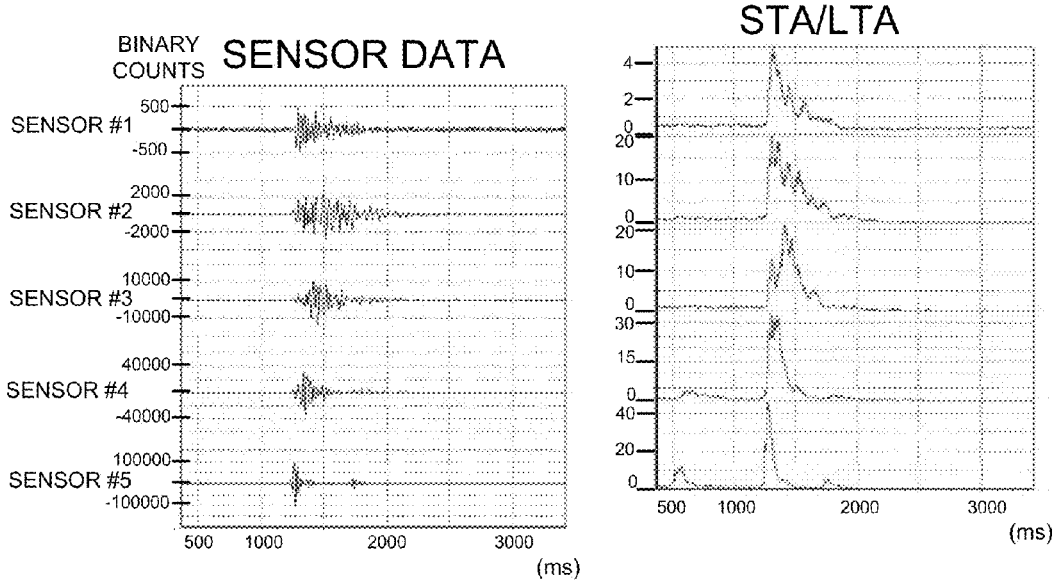
FIGS. 6A and 6B respectively depict typical digitized, time-stamped sensor data for a rock fall event and the corresponding STA/LTA ratio.

FIGS. 6A and 6B respectively depict typical digitized, time-stamped sensor data obtained at processor 120 for a rock fall event and the corresponding STA/LTA ratio. For the FIG. 6B plots, the STA duration a is 20 ms and the LTA duration b is 1000 ms. It can be seen from the FIGS. 6A and 6B plots that the rock fall event occurs around the 1250-1750 ms time period.

The STA/LTA ratio is useful for detecting when a signal changes to stand out from background noise and may therefore be compared against a suitable threshold to trigger the start and end of an event. For example, when the LTA/STA ratio is greater than an event start threshold (thresh_start), then processor 120 may determine that an event has started and the associated time $t_{start}$. Similarly, when an event has started and the LTA/STA ratio falls below an event end threshold (thresh_end), then processor 120 may determine that an event has ended and the associated time $t_{end}$. The STA/LTA threshold parameters thresh_start, thresh_end may be experimentally determined as a part of the calibration of system 10 and may depend, by way of non-limiting example, on the STA averaging duration a, the LTA averaging duration b, the spectral characteristics (e.g. amplitude and dominant frequencies) of the background noise in a vicinity of track section 12 and/or the expected spectral characteristics (e.g. amplitude and dominant frequencies) of an event that system 10 is designed to detect. These threshold parameters may additionally or alternatively be user adjustable.

The start and end times $t_{start}$, $t_{end}$ of an event can also be used to determine the event duration $t_{dur}$ as one of the FIG. 5 processing parameters 150 according to:

$$t_{dur} = t_{end} - t_{start} \quad (2)$$

An issue which may arise with the STA/LTA ratio is the so called "memory" associated with the LTA. The LTA value computed by processor 120 carries with it information about the last b samples (where b is the LTA duration used in equation (1)). In some cases, the last b samples will be influenced by an event. For example, when a train passes track section 12, it typically takes a period of time for the train to pass. In such cases, the last b samples used to compute the LTA may be influenced by the signal associated with the passing train—e.g. the LTA may be relatively large during, or even after, a passing train. In such circumstances, the relatively high LTA may cause the STA/LTA ratio to lose sensitivity, even if the STA is relatively high.

In some embodiments, therefore, processor 120 processes the data from data logger 110 to determine a modified STA/LTA ratio as one of processing parameters 150. This modified STA/LTA ratio may involve replacing the actual LTA with a constant c according to:

$$\left(\frac{STA}{LTA}\right)_{mod,n} = \frac{\sum_{i=(n-(a-1))}^{i=n} x_i}{c} \text{ where } n > a > 0 \quad (3)$$

The constant c may be representative of the LTA during event free times (e.g. times without rock fall or passing trains or the like) and, in some embodiments, may be determined during calibration of system 10. For example, the constant c may be determined in a relatively noise free period in the environment where system 10 is deployed prior to the actual deployment of system 10. In one particular embodiment, the constant c may be determined to be an actual LTA during such a noise free period (e.g. determined according to the denominator of equation (1)). The constant c may be user adjustable.

The modified STA/LTA ratio (equation (3)) may be used in substantially the same manner as the actual STA/LTA ratio (equation (1)) to determine the start and end of an event and the associated times $t_{start}$, $t_{end}$ and to determine the associated event duration $t_{dur}$. In some embodiments, the modified STA/LTA ratio may be used in addition to or as an alternative to the actual STA/LTA ratio. In some embodiments, the thresholding decision associated with the start and/or end of an event may involve a compound decision wherein both the modified and actual STA/LTA ratios are subject to threshold conditions. In some embodiments, the decision as to whether to use the actual STA/LTA ratio, the modified STA/LTA ratio or both (i.e. to determine the start and end of an event and the associated times $t_{start}$, $t_{end}$ and to determine the associated event duration $t_{dur}$) may be a user-selectable parameter.

Another processing parameter 150 that may be determined by processor 120 based on data from data logger 110 may be referred to as a peak particle velocity (PPV). The PPV may represent the magnitude of the sample with the largest absolute value during an event and may be determined according to:

$$PPV = MAX\{|x_i| | i \epsilon t_{start} \ldots t_{end}\} \quad (4)$$

where MAX{•} is an operator that returns the maximum value of the operand and $x_i$ represents the value of the $i^{th}$ sample.

As discussed above, in the illustrated embodiment, sensor arrays 18 comprise one or more acoustic energy sensors (e.g. sensors 50) which output signals 22 correlated with velocity of a sensor component. As such, the PPV corresponds to the maximum or peak velocity measured by such sensors—hence the term peak particle velocity. In general, however, sensor arrays 18 may comprise acoustic energy sensors which output signals 22 correlated with other parameters (e.g. energy, displacement and/or acceleration). In such embodiments, PPV should be understood to represent the magnitude of the sample with the largest absolute value during an event in accordance with equation (4) and need not represent velocity in strict sense. In some embodiments, processor 120 may also determine the time $t_{PPV}$ associated with the PPV. In some embodiments, processor 120 may also determine a global PPV value $PPV_{global}$ which represents the magnitude of the sample with the largest absolute value over all of the recorded samples—i.e. a PPV which is not limited to the times between $t_{start}$ and $t_{end}$ during an event.

System 10 may use PPV to help discriminate between significant rock falls and other types of events. In one particular embodiment, PPV is subjected to a thresholding process which may filter out small rock fall events, other low magnitude events (e.g. animals) and/or background noise events (e.g. the operation of a power generator). For example, if the PPV of an event is less than a PPV threshold (thresh_PPV), then processor 120 may determine that the event has insufficient magnitude to be a significant rock fall. The PPV threshold parameter thresh_PPV may be experimentally determined as a part of the calibration of system 10 and may depend, by way of non-limiting example, on particular minimum magnitude rock fall detection required of system 10, the expected magnitude of low magnitude events (e.g. animals or humans), the expected magnitude of background events (e.g. power stations, waterfalls, wind) and/or the like. The PPV threshold parameter thresh_PPV may additionally or alternatively be user adjustable.

Another processing parameter 150 that may be determined by processor 120 based on data from data logger 110 may be referred to as a the signal energy E. In some embodiments, the signal energy E used by system 10 may represent a windowed average of the sample amplitude squared and may be determined according to:

$$E_n = \frac{\sum_{i=n-(d-1)}^{n}(x_i)^2}{d} \quad (5)$$

where: $x_i$ represents the value of the $i^{th}$ sample, n is the index of the current sample $x_n$ and d is the window duration (number of samples). Examining equation (5), it will be appreciated that the duration d may be expressed as numbers of samples or equivalently as temporal durations.

Like the STA/LTA ratio discussed above, the signal energy E is useful for detecting when a signal changes to stand out from background noise and may therefore be compared against suitable thresholds to trigger the start and end of an event. For example, when the signal energy E is greater than an event start threshold (E_thresh_start), then processor 120 may determine that an event has started and the associated time $t_{start}$. Similarly, when an event has started and the signal energy E falls below an event end threshold (E_thresh_end), then processor 120 may determine that an event has ended and the associated time $t_{end}$. The threshold parameters E_thresh_start, E_thresh_end may be experimentally determined as a part of the calibration of system 10 and may depend, by way of non-limiting example, on the duration d of the energy window, the spectral characteristics (e.g. amplitude and dominant frequencies) of the background noise in a vicinity of track section 12 and/or the expected spectral characteristics (e.g. amplitude and dominant frequencies) of an event that system 10 is designed to detect. These threshold parameters may additionally or alternatively be user adjustable. The start and end times $t_{start}$, $t_{end}$ of an event can also be used to determine the event duration $t_{dur}$ as described above (equation (2)).

The signal energy E may also be used in addition to or in the alternative to the STA/LTA ratio in other circumstances where it might be appropriate to use the STA/LTA ratio. The maximum signal energy $E_{max}$=MAX$\{E_i | i \in t_{start} \ldots t_{end}\}$ also exhibits a correlation with the PPV discussed above. In some embodiments, the maximum signal energy $E_{max}$ may be used in addition to or in the alternative to the PPV value in circumstances where it might be appropriate to use the PPV value.

Another processing parameter 150 that may be determined by processor 120 based on data from data logger 110 is the spectral power distribution (e.g. frequency content) of a signal corresponding to an event. In one particular embodiment, processor employs a Fast Fourier Transform (FFT) technique to the sampled data during an event (i.e. between $t_{start}$ and $t_{end}$). The spectral power may therefore be referred to in this description as the FFT. As is known in the art, however, there are a number of FFT techniques and other techniques for determining the time-frequency content of a digitally sampled signal and any such techniques may be used to determine the time-frequency content of a signal.

Figures 6C, 6D:
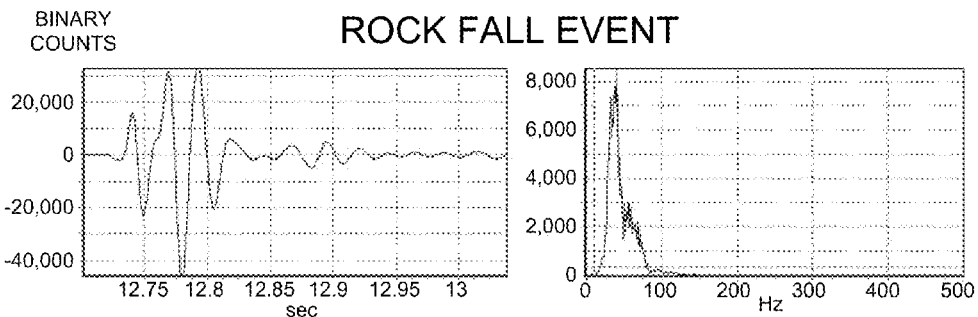
FIGS. 6C and 6D respectively show a 0.4 second segment of time stamped, digital sensor data and its corresponding FFT associated with a typical rock fall event.
Figures 6E, 6F:
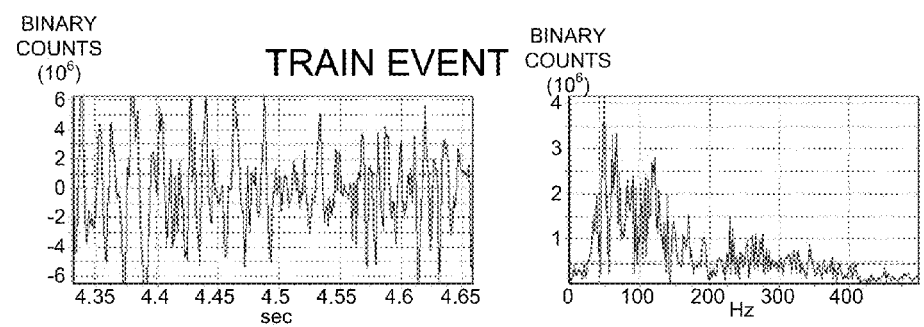
FIGS. 6E and 6F respectively show a 0.4 second segment of time stamped, digital sensor data and its corresponding FFT associated with a typical train event.
Figures 6G, 6H:
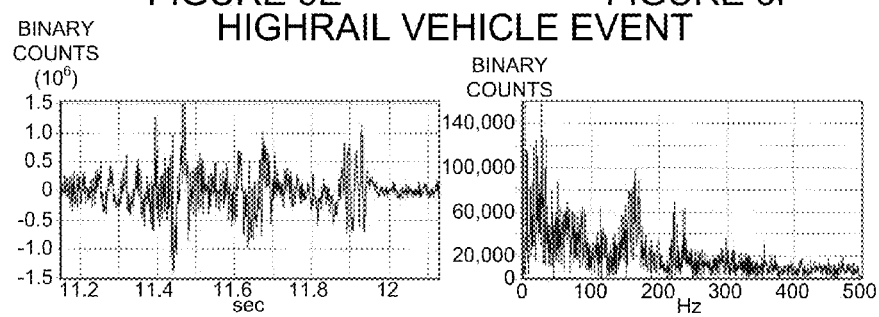
FIGS. 6G and 6H respectively show a 1.0 second segment of time stamped, digital sensor data and its corresponding FFT associated with a typical highrail vehicle event.

FIGS. 6C and 6D respectively show a 0.4 second segment of a time stamped, digital sensor signal received at processor 120 and a corresponding FFT associated with a typical rock fall event. FIG. 6D show that most of the spectral power of the digital sensor signals associated with a typical rock fall event is concentrated in the frequency band less than 125 Hz. FIGS. 6E and 6F respectively show a 0.4 second segment of a time stamped, digital sensor signal received at processor 120 and a corresponding FFT associated with a typical train event. FIG. 6F shows that the spectral power of the digital sensor signals associated with a typical train event is spread over 0-400 Hz and has significant power at frequencies over 200 Hz. FIGS. 6G and 6H respectively show a 1.0 second segment of a time stamped, digital sensor signal received at processor 120 and a corresponding FFT associated with a typical highrail vehicle event. FIG. 6H shows that the spectral power of the digital sensor signals associated with a typical highrail vehicle event (like a train event) is spread over 0-400 Hz and has significant power at frequencies over 200 Hz. The sensor data shown in FIGS. 6C-6H is obtained from representative rail sensors, but the inventors have concluded that similar results are achievable with suitably configured ballast sensors.

Figures 6I, 6J:
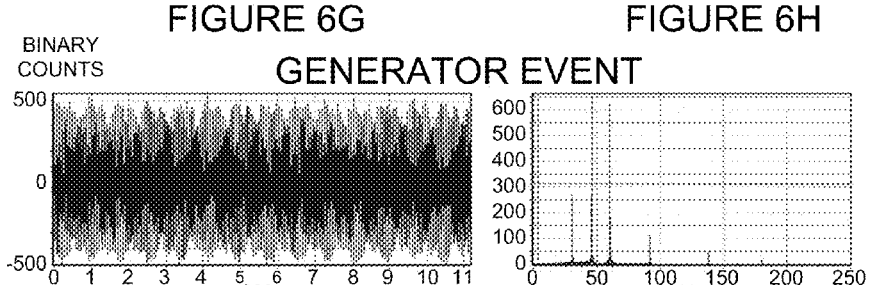
FIGS. 6I and 6J respectively show an 11 second segment of time stamped, digitized sensor data and its corresponding FFT associated with the operation of a generator in a vicinity of the FIG. 1 track section.

FIGS. 6I and 6J respectively show an 11 second segment of a time stamped, digital sensor signal received at processor 120 and a corresponding FFT associated with the operation of a generator in a vicinity of track section 12. FIG. 6J shows that the spectral power of the digital sensor signals associated with the generator has a unique frequency signature with harmonics at 30.66 Hz, 45.95 Hz and 60 Hz.

Figure 7A:
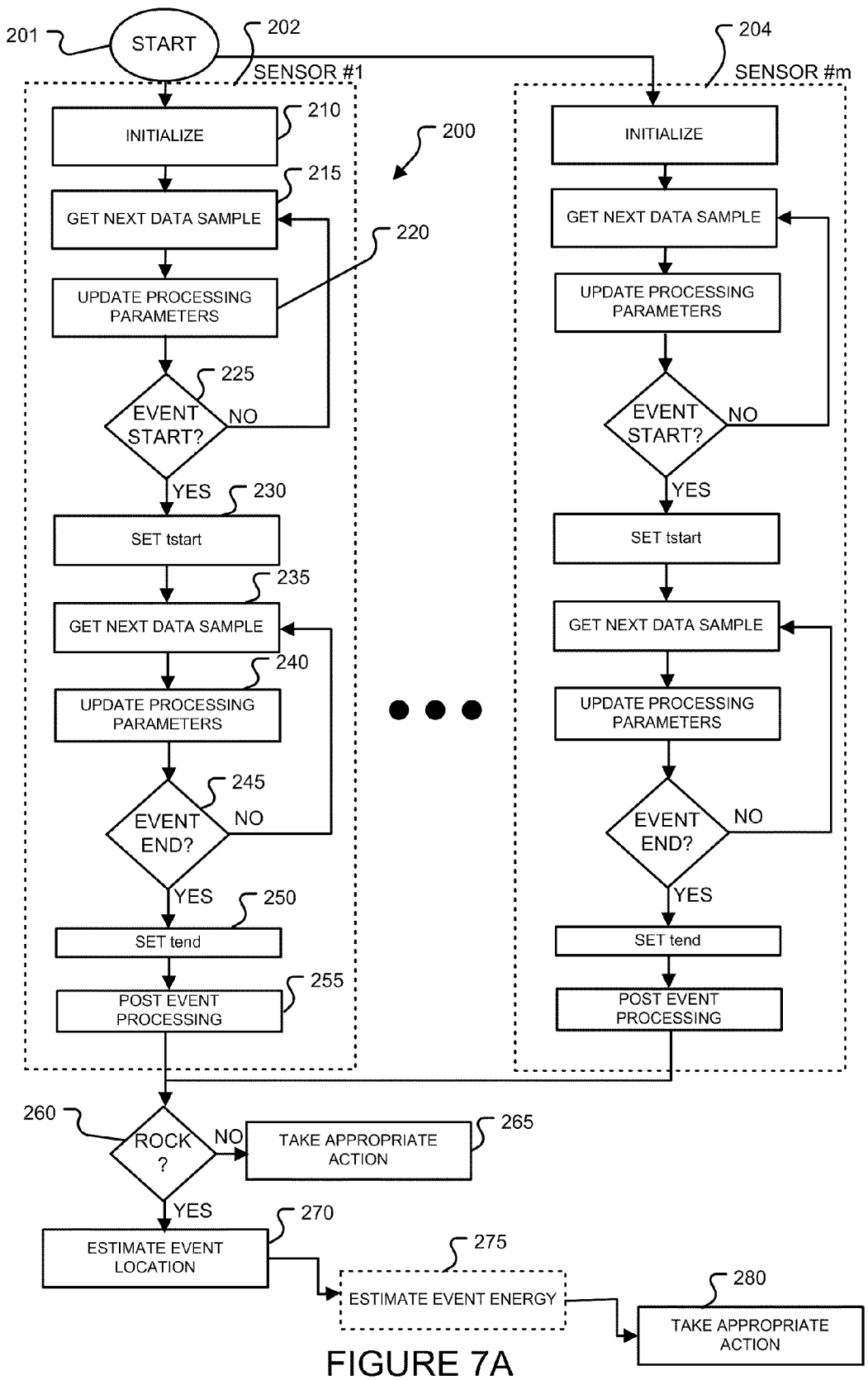
FIG. 7A schematically depicts a method for event detection method according to a particular embodiment.

FIG. 7A schematically depicts a method 200 for event detection according to a particular embodiment. Method 200 may be performed in whole or in part by embedded processor 120. Method 200 may make use of data obtained from data logger 110 and/or DAU 116 and may also make use of processing parameters 150. As discussed above, in other embodiments, rock fall detection (including method 200 in whole or in part) may be performed by other processors, such as by processors associated with remote workstation 30 and/or other systems 32.

Method 200 starts at block 201. Method 200 may involve a number of procedures which are similar for the data associated with each sensor—e.g. to each particular digital sensor signal 108 (FIG. 3). In the illustrated embodiment, these similar procedures are shown by the representative procedures of block 202 (associated with sensor #1) and block 204 (associated with sensor #m). It will be appreciated that, depending on the number of sensors and the corresponding number of digital sensor signals 108, method 200 may generally comprise any suitable number of procedures similar to those of blocks 202, 204. The procedure of block 202 is now described in more detail, it being understood that the procedure associated with block 204 and other similar blocks may be substantially similar to that of block 202.

The block 202 procedure starts in block 210 which involves initializing a number of parameters. For example, block 210 may involve obtaining sufficient number of data samples (a) to calculate the STA (the numerator of equation (1) and/or equation (3)) and/or a sufficient number of data samples (b) to calculate the LTA (the denominator of equation (1)). Such data samples may be taken from the digital signal sensor signal 108 associated with block 202. Block 210 may involve resetting a number of the processing parameters 150 which may have been used during previous post event processing (described in more detail below). Block 210 may also involve initializing one or more calibration parameters and/or user-configurable parameters. The procedure of block 202 then proceeds to block 215, which involves obtaining the next data sample—e.g. the next data sample from the digital sensor signal 108 associated with block 202.

In block 220, block 202 may involve updating one or more processing parameters 150 based on the newly acquired block 215 data and, in some instances, the historical data obtained prior to the current iteration of block 215. In particular embodiments, the particular processing parameters 150 which are updated in block 215 include those associated with event-start triggering criteria. As explained above, processing parameters 150 associated with triggering the start of an event may include: the STA/LTA ratio (equation (1)), the modified STA/LTA ratio (equation (3)) and/or the energy (equation (5)).

Block 225 involves evaluating event-start criteria. The block 225 event-start criteria may involve an evaluation of whether one or more processing parameters (e.g. the STA/LTA ratio (equation (1)), the modified STA/LTA ratio (equation (3)) and/or the energy (equation (5)) are greater than one or more corresponding event-start thresholds (e.g. thresh_start$_{(STA/LTA)}$, thresh_start$_{(STA/LTA)mod}$, thresh_start$_{(E)}$. If the block 225 evaluation of the event-start criteria is negative (block 225 NO output), then the procedure of block 202 loops back to block 215 to obtain another data sample. If on the other hand the block 225 evaluation of the event-start criteria is positive (block 225 YES output), then the procedure of block 202 proceeds to block 230.

Block 230 involves setting a value for $t_{start}$. In particular embodiments, the block 230 $t_{start}$ value may be based on the time associated with the current block 215 data sample. The procedure of block 202 then proceeds to blocks 235 and 240 which involve obtaining the next data sample and updating one or more processing parameters in a manner similar to that of blocks 215 and 220 described above.

Block 245 then involves evaluating event-end criteria. The block 245 event-end criteria may involve an evaluation of whether one or more processing parameters (e.g. the STA/LTA ratio (equation (1)), the modified STA/LTA ratio (equation (3)) and/or the energy (equation (5)) are less than one or more corresponding event-end thresholds (e.g. thresh_end$_{(STA/LTA)}$, thresh_end$_{(STA/LTA)mod}$, thresh_end$_{(E)}$. If the block 245 evaluation of the event-end criteria is negative, then the block 202 procedure loops back to block 235 to obtain another data sample. If on the other hand the block 245 evaluation of the event-end criteria is positive, then block 202 procedure determines that the event has ended and proceeds to block 250, which involves setting a value for the event end time $t_{end}$. In particular embodiments, the block 250 $t_{end}$ value may be based on the time associated with the current block 235 data sample.

In the illustrated embodiment, the block 202 procedure then proceeds to block 255, which involves post event processing. The post event processing of block 255 may involve discriminating between types of events or otherwise determining whether a particular event is a significant rock fall event. In the illustrated embodiment of method 200, the block 255 post event processing is shown within the block 202 procedure—i.e. the block 255 post event processing may be performed for each sensor whose digital signal 108 triggers the detection of an event. This is not necessary. In some embodiments, the block 255 post event processing may be performed outside of the block 202 procedure—e.g. the block 255 post event processing may be performed on a global basis and/or for a subset of the sensors whose digital signals 108 trigger the detection of an event.

Figure 7B:
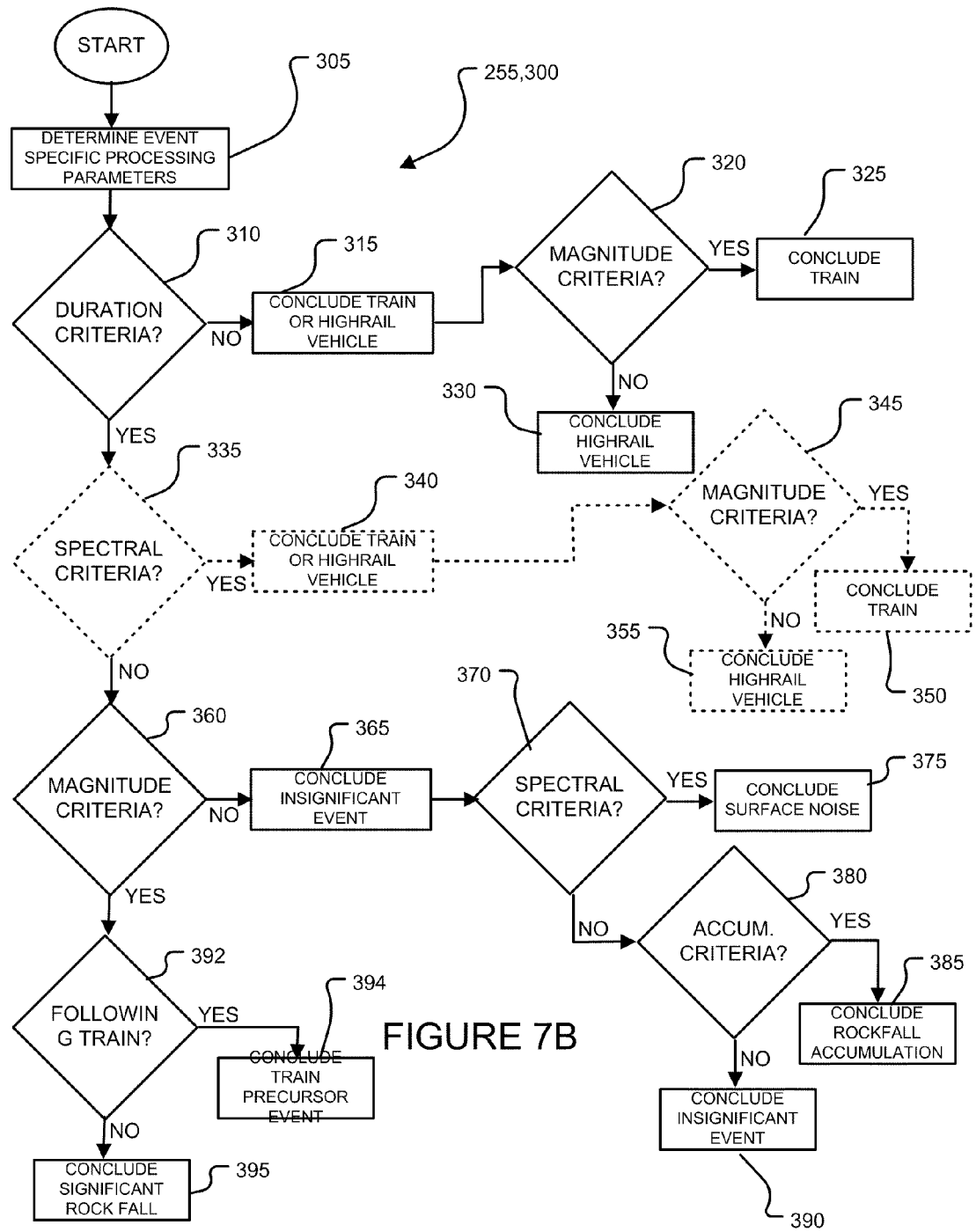
FIG. 7B schematically depicts a method for post event processing which may be performed as a part of the FIG. 7A event detection method according to a particular embodiment.

FIG. 7B schematically depicts a method 300 for post event processing which may be performed in block 255 according to a particular embodiment. In the illustrated embodiment, the post event processing of method 300 involves discriminating between a number (e.g. six) of different types of events. In other embodiments, the post event processing may involve discriminating between two types of events—i.e. significant rock fall events and any other kind of event. In some embodiments, method 300 may be performed for each sensor whose digital sensor signal 108 triggers the detection of an event. In other embodiments, method 300 may be performed for a subset of the sensors whose digital sensor signals 108 trigger the detection of an event.

In the illustrated embodiment, method 300 starts in block 305 which involves determining one or more event specific processing parameters 150. Once $t_{start}$ and $t_{end}$ are determined (eg. in blocks 230, 250) for a particular sensor in system 10, processor 120 may obtain a subset of the associated digital sensor signal 108 which occurs between $t_{start}$ and $t_{end}$. This data subset may in turn be processed to obtain the block 305 event specific processing parameters 150. Examples of event specific processing parameters that may be determined in block 305 include: the duration $t_{dur}$ of the event which may be determined according to equation (2); the PPV which may be determined according to equation (4); the time ($t_{PPV}$) associated with the PPV; the spectral power (FFT) of the discrete signal between $t_{start}$ and $t_{end}$. To the extent that the STA/LTA ratio, the modified STA/LTA ratio or the energy are not determined in the block 202 procedure, then any one or more of these quantities (and/or their associated maxima, STA/LTA$_{max}$, STA/LTA$_{mod\_max}$, $E_{max}$ and the times of their associated maxima) may also be determined in block 305.

Method 300 then proceeds to block 310 which involves evaluating event duration criteria. The block 310 evaluation may involve comparing the event duration $t_{dur}$ to a threshold (thresh_dur) to determine whether the event duration $t_{dur}$ is less than the threshold (thresh_dur). In some embodiments, the event duration threshold (thresh_dur) may be in a range of 1-3 seconds. In other embodiments, this range may be 2-10 seconds. The magnitude of the event duration threshold (thresh_dur) may depend on the typical length of the trains that pass through track section 12.

If $t_{dur}$ is greater than the event duration threshold (thresh_dur), then method 300 may proceed along the block 310 NO output to block 315. In the illustrated embodiment, block 315 involves concluding that the event is either a passing train or a passing highrail vehicle. From block 315, method 300 proceeds to block 320 which involves an evaluation of a magnitude criteria to determine whether the event was triggered by a passing train (block 320 YES output and the conclusion of block 325) or the event was triggered by a highrail vehicle (block 320 NO output and the conclusion of block 330). The block 320 magnitude evaluation may involve comparing the PPV of the associated digital sensor signal 108 to a suitable threshold. If the PPV is greater than the block 320 threshold, then the event is determined to be a train (block 320 YES output and block 325 conclusion), whereas if the PPV is less than the block 320 threshold, then the event is determined to be a highrail vehicle (block 320 NO output and block 330 conclusion). Depending on the geological site conditions, in some embodiments block 320 may additionally or alternatively involve an evaluation of spectral criteria (e.g. comparing the FFT of an event to one or more thresholds). Such spectral criteria may be used as an alternative to or in addition to the block 320 magnitude criteria to discriminate a train event from a highrail event.

Returning to the block 310 evaluation, if $t_{dur}$ is less than the event duration threshold (thresh_dur), then method 300 may proceed along the block 310 YES output to optional block 335. Block 335 involves the optional evaluation of spectral criteria to determine whether an event was triggered by a passing train or highrail vehicle. As discussed above, depending on the geological conditions in a vicinity of track section 12, suitably configured sensors (e.g. ballast sensor 50 of FIG. 2A and/or rail sensor 80 of FIG. 2B) may generate distinctive frequency characteristics in response to trains and/or highrail vehicles traveling on track section 12. These distinctive frequency characteristics may be used to discriminate trains or highrail vehicles from other types of events. In one particular embodiment, the block 335 spectral criteria involves determining whether the FFT associated with a digital sensor signal 108 has a significant amount (e.g. x % or more) of its power at frequencies greater than a frequency threshold (thresh_freq). In one particular embodiment, this threshold may be in a range of 100 Hz-300 Hz. In another embodiment, this threshold may be in a range of 125 Hz-200 Hz. In one particular embodiment, the significant amount (e.g. x % or more) may be in a range of 0%-25%. In other embodiments, the significant amount (e.g. x % or more) may be in a range of 5%-15%.

If the FFT of the rail sensor has a significant amount (e.g. x % or more) of its power at frequencies greater than a frequency threshold (thresh_freq), then the block 335 evaluation is positive (YES output) and method 300 proceeds to block 340 which involves concluding that the event is either a passing train or a passing highrail vehicle. Blocks 340, 345, 350 and 355 may be substantially similar to blocks 315, 320, 325 and 330 discussed above and may involve discriminating between a train (block 350 conclusion) and a highrail vehicle (block 355 conclusion).

If, on the other hand, the FFT of the rail sensor does not have a significant amount (e.g. x % or more) of its power at frequencies greater than a frequency threshold (thresh_freq), then the block 335 evaluation is negative (NO output) and method 300 proceeds to block 360 which involves evaluation of magnitude criteria to determine whether the event in question is a significant rock fall event—i.e. a rock fall event worthy of concern. The block 360 magnitude evaluation may involve comparing the PPV of the associated digital sensor signal to a suitable threshold (thresh_PPV). In some embodiments, this magnitude threshold (thresh_PPV) may be in a range of 500-5000 bits. In other embodiments, this range may be 750-2,500 bits. If the PPV is less than the block 360 threshold (thresh_PPV), then the event is determined to be an insignificant event (block 360 NO output and block 365 conclusion).

In the illustrated embodiment, however, method 300 goes beyond the block 365 conclusion of classifying the event as an insignificant event. As discussed above, it may be desirable to discriminate other types of natural or human-made noise that may trigger events in a vicinity of track section 12. In one particular embodiment, a generator (not shown) is located in a vicinity of track section 12. When the generator turns on, it may trigger an event on one or more sensors of system 10. In the illustrated embodiment, method 300 proceeds from block 365 to block 370 which involves evaluation of spectral criteria. As explained above, the spectral power associated with the start up and operation of the generator has a particular spectral pattern. Accordingly, spectral criteria can be designed for the block 370 inquiry to determine whether the event was triggered by the generator. Such spectral criteria may involve evaluation of whether the FFT of the associated digital sensor signal 108 has a significant amount (e.g. y % or more) of its power at frequencies within particular frequency bands associated with the start up and operation of the generator. If the block 370 evaluation is positive (block 370 YES output), then method 300 concludes that the event was triggered by the generator in block 375.

It should be noted that the block 370 spectral evaluation and the block 375 conclusion that the event was triggered by a generator represent one non-limiting example of the type of criteria which may be used to discriminate other types of natural or human-made surface noise that may trigger events in a vicinity of track section 12. In other embodiments, it might be desirable to use additional or alternative criteria (e.g. in block 370 or in other similar inquiries) to discriminate additional or alternative surface noise events. Such surface noise events may include (by way of non-limiting example): noise created by moving water (e.g. waterfalls, rivers or the like); noise created by animals; noise created by nearby traffic; noise created by falling trees; noise created by trains or highrail vehicles that have come to a stop in a vicinity of track section 12; and/or the like. The types of criteria used to discriminate these events may include (by way of non-limiting example): magnitude criteria, spectral criteria, duration criteria, correlation criteria and/or the like. It is not necessary that the evaluation of these additional or alternative criteria occur in any particular order relative to the other method 300 criteria evaluations. In general, the method 300 criteria evaluations can occur in any desirable order. For example, if it is known that the generator is likely to start every 10 minutes and run for 2 minutes, then it may be desirable to locate the block 370 spectral criteria evaluation at an earlier point within method 300 to quickly conclude generator events and to thereby conserve processing resources.

If the block 370 evaluation is negative (block 370 NO output), then method 300 proceeds to block 380 which involves an evaluation of accumulation criteria to determine whether there has been a sufficient amount of low magnitude rock fall within a sufficiently short period to time to conclude that there has been rock fall accumulation that may be of concern. In one particular embodiment, the block 380 accumulation criteria involves consideration of whether method 300 has reached block 380 (i.e. small rock fall event) more than a threshold number of times (thresh_#) within a recent time period ΔT. By way of non-limiting example, block 380 may involve evaluating whether method 300 has reached block 380 more than 5 times within the last hour. In some embodiments, the block 380 threshold number of times (thresh_#) is in a range of 3-50. In other embodiments, this range is 10-20. In some embodiments, the block 380 time period ΔT is in a range of 30-900 minutes. In other embodiments, this range is 60-480 minutes.

If the block 380 accumulation criteria evaluation is positive (block 380 YES output), then method 300 proceeds to block 385 which concludes that there has been sufficient rock fall accumulation to be of concern. If the block 390 accumulation criteria evaluation is negative (block 380 NO output), then method 300 proceeds to block 390 which concludes that the event was an insignificant rock fall event.

Returning to the block 360 magnitude evaluation, if the PPV is greater than the block 360 threshold (thresh_PPV), then method 300 proceeds (via block 360 YES output) to block 392 which involves an inquiry into whether the current event is followed by a train event. The inventors have determined that when a train passes over track section 12, the passing train can trigger a number of events (e.g. the train can satisfy the block 225 event start criteria) prior to triggering the principal train event. These events which are triggered prior to the principal train event may be referred to as train precursor events.

Figure 8:
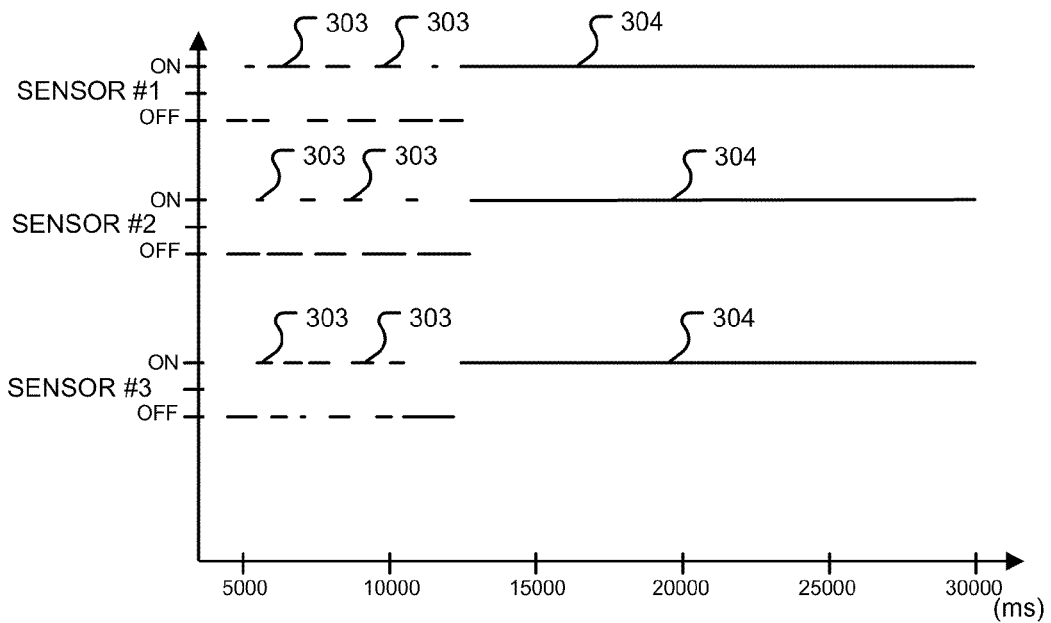
FIG. 8 is a schematic depiction of the triggered state of a number of sensors in the FIG. 1 rock fall detection system in response to a passing train.

FIG. 8 is a schematic depiction of the triggered state of a number of sensors in response to a passing train. It can be seen from FIG. 8, that a number of train precursor events 303 occur for each sensor in the time leading up to the persistent principal train events 304. The inventors have determined that the time during which train precursor events are likely to occur is within a time window $\Delta t_{pre-train}$ prior to the onset of principal train events. In some embodiments, this time window $\Delta t_{pre-train}$ is in a range of 5-30 seconds. In other embodiments, this time window $\Delta t_{pre-train}$ is in a range of 10-20 seconds.

In some embodiments, the block 392 inquiry as to whether the event is followed by a train event may involve an inquiry into whether the current event being processed in method 300 is followed within a time window $\Delta t_{pre-train}$ by a persistent train event. As discussed herein, a persistent train event can be discriminated on the basis of duration criteria (e.g. block 310), spectral criteria (e.g. block 335), magnitude criteria (e.g. block 320, block 330), cross-correlation criteria, or any suitable combination thereof. If the block 392 inquiry is positive (e.g. the current event is followed by a train event within the time window $\Delta t_{pre-train}$ block 392 YES output), then method 300 proceeds to block 394 which involves concluding that the current event is a train precursor event. If, on the other hand, the block 392 inquiry is negative (e.g. the current event is not followed by a train event within the time window $\Delta t_{pre-train}$—block 392 NO output), then method 300 proceeds to block 395, where the current event is determined to be a significant rock fall event.

As discussed above, method 300 (FIG. 7B) represents one possible embodiment of block 255 of method 200 (FIG. 7A). Returning to FIG. 7A, at the conclusion of block 255 (e.g. method 300), method 200 proceeds to block 260 which involves an inquiry into whether the block 255 post event processing associated with any of the sensors reached a conclusion that the event was a rock fall event (e.g. either the block 390 conclusion of method 300 that the event is an insignificant rock fall event and/or the block 395 conclusion of method 300 that the event is a significant rock fall event). If the event was not a rock fall event (block 260 NO output), then method 200 proceeds to block 265 which involves taking appropriate action for a non-rock fall event.

The nature of the block 265 action may depend on whether any of the non-rock fall events are considered to be important for some reason. The block 265 action may comprise logging the non-rock fall event or doing nothing. In one particular embodiment, the block 265 action may involve generating an event record associated with the non-rock fall event. The record of the non-rock fall event may include recordal of a number of parameters associated with the event. In particular embodiments, the block 265 record may include one or more of: the event type (e.g. a block 325, 350 train event, a block 330, 355 highrail vehicle event or a block 375 surface noise event); a number of triggered sensors; start and end times of the event which may include the start time ($t_{start}$) for the first triggered sensor and the end time ($t_{end}$) for the last sensor to remain triggered; the PPV and the associated time $t_{PPV}$ for each triggered sensor; the maxima (and associated times) of one or more other block 305 event specific parameters (e.g. $STA/LTA_{max}$, $E_{max}$ or the like); and any other parameter of which data processor 120 may be aware. In some embodiments, the block 265 record may also include one or more of the images of track section 12 which may be captured by cameras 34.

In some embodiments, block 265 may involve storing the event record in local memory (e.g. in data logger 110, memory 128 and/or image data memory 130) until such time as signal processing unit 26 is polled for events (e.g. by remote workstation 30 over network connection 28). Depending on the availability of local memory, in other embodiments, block 265 may involve transmitting the event record (e.g. to remote workstation 30 over network connection 28) for remote storage.

Figure 7C:
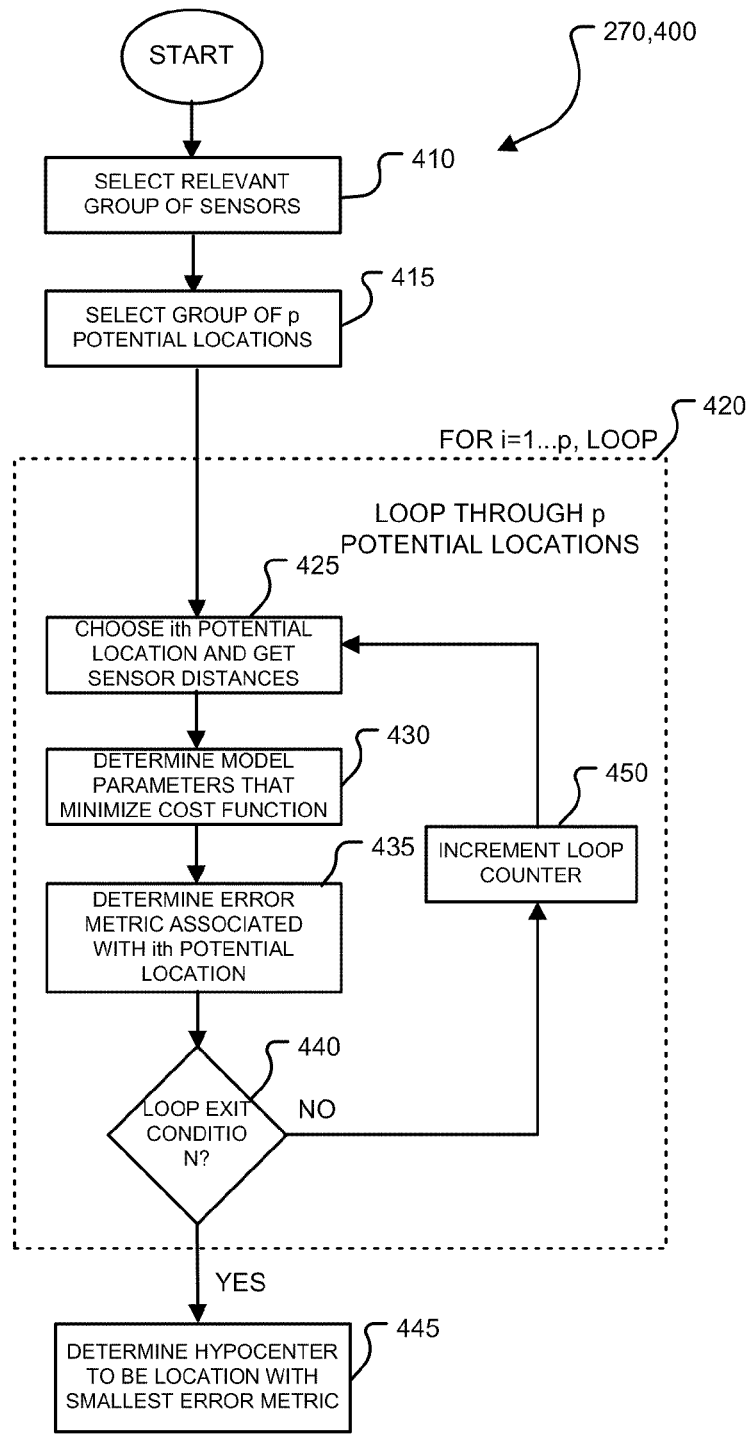
FIG. 7C schematically depicts a method for estimating a location of a rock fall event which may be performed as a part of the FIG. 7A event detection method according to a particular embodiment.

If, on the other hand, the event was a rock fall event (block 260 YES output), then method 200 proceeds to block 270 which involves estimating a location of the rock fall event. Block 270 may involve estimating a location of the rock fall event with a degree of accuracy which is finer than the minimum spacing 20 between sensor arrays 18 of system 10 (see FIG. 1). FIG. 7C schematically depicts a method 400 for estimating a location of a rock fall event which may be performed in block 270 according to a particular embodiment. Method 400 commences in block 410 which involves selecting a group of sensors to be considered for estimating the rock fall location. In some embodiments, block 410 may involve determining the group of sensors to include all triggered sensors whose start times $t_{start}$ are within a time window $\Delta T_{start}$ of the start time $t_{start}$ of a first sensor to trigger on a rock fall event.

Figure 9A:
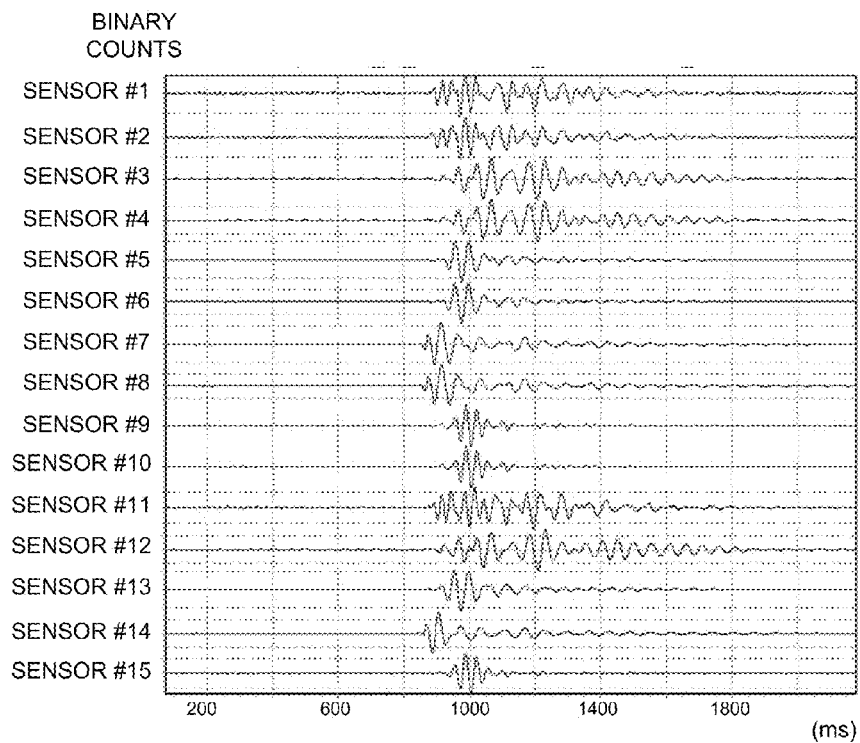
FIG. 9A shows a typical response of a number of sensors of the FIG. 1 rock fall detection system to a rock fall event.
Figure 9B:
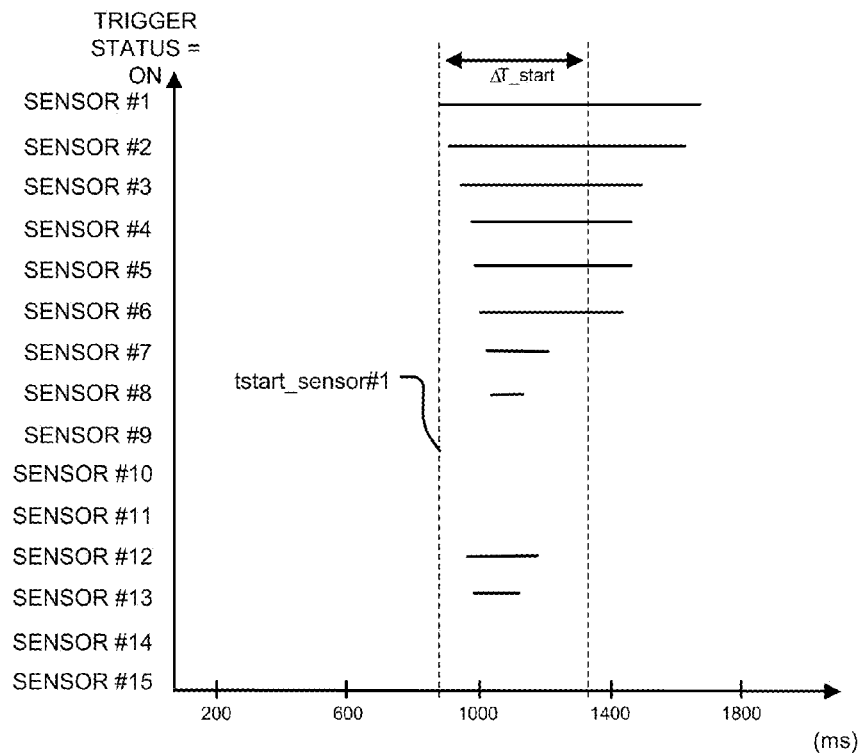
FIG. 9B is a schematic depiction of the triggered state of the FIG. 9A sensors.

This block 410 determination is shown schematically in FIGS. 9A and 9B. FIG. 9A shows a typical response of a number of sensors to a rock fall event. Like FIG. 4E, the vertical axis of FIG. 9A plot is measured in binary counts and the horizontal axis is measured in milliseconds. It will be noted that the plots for the individual sensor signals shown in FIG. 9A are on different vertical scales, but that the particular scales for each sensors are omitted for clarity. FIG. 9A also contrasts with FIG. 4E in that FIG. 9A is shown on a much smaller time scale—i.e. FIG. 4E spans a time period of 30 s, whereas FIG. 9A spans a time period of 2.2 s.

For each sensor of the FIG. 9A plot, FIG. 9B shows when the sensor is triggered—i.e. when the sensor's trigger status is ON. It can be seen from FIG. 9A, that the sensor #1 is the first to trigger (at $t=t_{start\_sensor\#1}$). Because acoustic waves take time to travel through the substrate in the region of track section 12, it may be assumed that sensor #1 is closest to the hypocenter of the rock fall event. The block 410 process for selecting the group of sensors to be considered for estimating the rock fall location may involve selecting all of the sensors which are triggered within a time window $\Delta T_{start}$ of $t_{start\_sensor\#1}$.

This time window $\Delta T_{start}$ is shown in FIG. 9B. It can be seen from FIG. 9B that sensors #2-8 and #12-13 are also triggered within this time window $\Delta T_{start}$. Accordingly, block 410 may involve selecting sensors #1-8 and #12-13 to be the sensors used for estimating the rock fall location. FIG. 9B also shows that sensors #9-11 and #14-15 are not triggered. As such, sensors #9-11 and #14-15 are not selected for estimating the rock fall location in accordance with the illustrated embodiment. Although not explicitly shown in FIG. 9B, sensors which are triggered after the time window $\Delta t_{start}$ may be assumed to be indicative of a different event.

The block 410 time window $\Delta T_{start}$ may be related to a prediction of the average speed of acoustic waves in the earth near track section 12 and the length of track section 12 being considered. For example, if the length of track section 12 being monitored is 1 km and the average speed of acoustic waves in the substrate near track 12 is determined to be 300 m/s, then the block 410 time window $\Delta T_{start}$ may be set to be 3.3 seconds.

Once the block 410 group of sensors is selected method 400 (FIG. 7C) proceeds to block 415 which involves selecting a group of p potential locations for the hypocenter of the rock fall event. The p potential hypocenter locations may be spaced apart from one another by a suitable interval d which depends on the location detection accuracy desired from system 10. The number p of potential hypocenter locations may depend, for example, on the processing resources associated with system 10 (e.g. associated with embedded processor 120). As discussed above, it is logical to assume that the hypocenter of the rock fall may be most proximate to the sensor that triggers first (e.g. sensor #1 in the exemplary circumstance of FIGS. 9A and 9B). In particular embodiments, the group of p potential hypocenter locations may be provided in a grid around the location of the sensor that is triggered first and the grid may have a spacing of d between potential locations. In some embodiments, the spacing d may be in a range of 1-20 m. In some embodiments, this spacing d is in a range of 2-5 m. In some embodiments, the number p of potential hypocenter locations is in a range of 5-100. In some embodiments, this number p of potential hypocenter locations is in a range of 10-25.

Method 400 then proceeds to loop 420. Loop 420 involves carrying out a number of procedures for each of the p potential hypocenter locations determined in block 415. In the illustrated embodiment, loop 420 is indexed by the variable i, which may be referred to as the loop counter. The loop counter i starts at i=1 on the first iteration of loop 420 and is incremented by one for each iteration of loop 420 until i=p at which point, method 400 exits from loop 420. Loop 420 commences in block 425 which involves selecting the $i^{th}$ potential hypocenter location and determining the distances $x_i$ between the $i^{th}$ potential hypocenter location and the locations of the block 410 sensors. It will be appreciated that where the block 410 group of sensors includes N sensors, then the quantity $x_i$ will be a 1×N vector quantity having the form $[x_{1\_i}, x_{2\_i} \ldots x_{N\_i}]^T$ where the notation $x_{j\_i}$ indicates the distance between the $j^{th}$ sensor and the $i^{th}$ potential hypocenter location. Once the location of the $i^{th}$ potential hypocenter location is known, the distances $x_i$ may then be determined based on pre-calibrated or otherwise known locations of the sensors of system 10.

Method 300 then proceeds to block 430 which involves determining model parameters. In one particular embodiment, the spatial attenuation of the PPV of a rock fall event is modeled according to an exponential decay model:

$$y(x) = Ae^{-Bx} \quad (6)$$

where: $y(x)$ represents the PPV amplitude at a distance x from the hypocenter of the rock fall event, A is a model parameter representative of the PPV at the hypocenter and B is an absorption coefficient model parameter which may be representative of a quality factor of the substrate in the region of track section 12. In accordance with the above described notation, model equation (6) may be rewritten as:

$$y_{j\_i} = A_i e^{-B_i x_{j\_i}} \quad (7)$$

where: $y_{j\_i}$ is the expected PPV of the $j^{th}$ sensor based on a rock fall at the $i^{th}$ potential hypocenter, $x_{j\_i}$ is the distance between the $j^{th}$ sensor and the $i^{th}$ potential hypocenter location, $A_i$ is a model parameter representative of the PPV at the $i^{th}$ potential hypocenter and $B_i$ is an absorption coefficient model parameter for the $i^{th}$ potential hypocenter which may be representative of a quality factor of the substrate in the region of track section 12. In other embodiments, other models may be used for the spatial attenuation of the PPV.

Block 430 then involves solving for the model parameters by minimizing a cost function. In embodiments which make use of the model of equations (6) and (7), the model parameters to be determined in block 430 are the quantities $A_i$ and $B_i$. It will be appreciated that in embodiments which use other attenuation models, the model parameters to be determined may be different. In one particular example embodiment, the cost function used in block 430 is a least squares cost function which, for the $i^{th}$ potential hypocenter location, may be given by:

$$F_i \sum_{j=1}^{N} w_{j\_i}(r_{j\_i})^2 = \sum_{j=1}^{N} w_{j\_i}(y_j - A_i e^{-B_i x_{j\_i}})^2 \quad (8)$$

where: $F_i$ is the cost function for the $i^{th}$ potential hypocenter location, N is the number of block 410 sensors, $w_{j\_i}$ is an optional weighting coefficient for the $j^{th}$ sensor and the $i^{th}$ potential hypocenter location, $y_j$ is the actual sensor PPV for the $j^{th}$ sensor and the quantity $$r_{j\_i} = y_j - A_i e^{-B_i x_{j\_i}}$$

is referred to as the residual for the $j^{th}$ sensor and the $i^{th}$ potential hypocenter location.

The cost function of equation (8) can be minimized when:

$$\frac{\partial F_i}{\partial A} = 0 \text{ and} \quad (9a)$$

$$\frac{\partial F_i}{\partial B} = 0 \quad (9b)$$

Equations (9a) and (9b) can be solved for the $i_{th}$ potential hypocenter location to yield the parameters $A_i$ and $B_i$.

Solving equations (9a) and (9b) is a non-linear problem which may be simplified (e.g. linearized) by taking the natural logarithm of both sides of equation (7) to yield:

$$\ln(y_{j\_i}) = \ln(A_i) - B_i x_{j\_i} = y'_{j\_i} = A'_i - B_i x_{j\_i} \quad (10)$$

where $y'_{j\_i} = \ln(y_{j\_i})$ and $A'_i = \ln(A_i)$. Equation (10) represents a linear regression model (as opposed to the exponential regression model of equation (7)) and may be used to create a least squares cost function, which in turn may be minimized to yield the quantities $A'_i$ and $B_i$. The parameter $A_i$ may then be obtained according to $A_i = e^{A'_i}$. Minimizing a least squares cost function for a linear regression model has a closed form solution and is well understood by those skilled in the art.

Examining the equation (6) model more closely, it can be seen that the quantity A depends on the amplitude of an event wavelet at the hypocenter and therefore varies from event to event. In contrast, the quantity B represents a quality factor which may depend on the geotechnical characteristics of the environment around track section 12. It would be expected, therefore, that the quantity B is relatively constant from event to event. The inventors have experimentally determined (using the least squares curve fitting techniques described above) that the parameter B for a particular track section 12 typically stays within 5-10% of some average value $B_o$. Accordingly, in some embodiments, the quantity $B_o$ may be determined during calibration and thereafter the parameter $B_i$ may be taken as a constant $B_i=B_o$. In such embodiments, equations (8) and (9a) may be used to solve for $A_i$, which is given by:

$$A_i = \frac{\sum_{j=1}^{N} w_{j\_i} y_j e^{-B_0 x_{j\_i}}}{\sum_{j=1}^{N} w_{j\_i} e^{-2B_0 x_{j\_i}}} \quad (11)$$

For the equation (6) attenuation model, at the conclusion of block 430, method 400 has determined the model parameters $A_i$ and $B_i$ for the $i^{th}$ potential hypocenter location. For other models, block 430 may yield different model parameters for the $i^{th}$ potential hypocenter location. Method 400 then proceeds to block 435 which involves determining an error metric associated with the $i^{th}$ potential hypocenter location. In general, the block 435 error metric may be any suitable quantity that is representative of the error associated with the model parameters determined in block 430 for the $i^{th}$ potential hypocenter. The block 435 error metric may involve a summation of constituent error metrics over the N block 410 sensors. Each constituent error metric may involve a difference between the PPV predicted by the loop 420 model and the PPV measured by the sensor. In embodiments which make use of a least squares cost function (e.g. equation (8)), the block 435 error metric ($E_i$) may comprise a sum of the squares of the residuals for the $i^{th}$ potential hypocenter location over the N block 410 sensors which may be given by:

$$E_i \sum_{j=i}^{N} (r_{j\_i})^2 \quad (12)$$

in embodiments which make use of the regression model of equation (7), equation (12) becomes:

$$E_i \sum_{j=1}^{N} (y_j - y_{j\_i})^2 \quad (13)$$

where $y_j$ is the PPV value measured at the $j^{th}$ sensor and $y_{j\_i}$ is the PPV value predicted by model equation (7) for the $j^{th}$ sensor and the $i^{th}$ potential hypocenter location.

Once the block 435 error metric ($E_i$) is determined, method 400 proceeds to block 440 which involves evaluation of a loop exit condition. If there are other potential hypocenter locations in the block 415 group of p potential hypocenter locations which have yet to be examined, then the block 440 inquiry is negative (NO output) and method loops back to block 450, where the loop counter i is incremented to refer to the next potential hypocenter location and then back to block 425. If the procedures of blocks 425, 430 and 435 have been performed for all of the block 415 group of p potential hypocenter locations, then the block 440 loop exit condition is fulfilled (YES output) and method 400 proceeds to block 445.

Block 445 involves selecting one of the block 415 group of potential hypocenters to be the estimated hypocenter of the rock fall event. In the illustrated embodiment, the block 445 selection is based on the hypocenter having the lowest error metric (as determined in block 435). In embodiments which use the error metric of equation (12) or (13), block 445 involves selecting the estimated location of the hypocenter of the rock fall event to be the potential hypocenter having the lowest value of $E_i$.

In other embodiments, method 400 may be implemented with a different attenuation model. For example, in one alternative embodiment, the attenuation model of equation (6) may be replaced by the following model:

$$y(x) = \frac{Ae^{-Bx}}{\sqrt{x}} \quad (14)$$

which represents a combination of absorption and geometric spreading. For the equation (14) model, the equivalent to equation (7) is:

$$y_{j\_i} = \frac{A_i e^{-B_i x_{j\_i}}}{\sqrt{x_{j\_i}}} \quad (15)$$

the least squares cost function equivalent to equation (8) is:

$$F_i \sum_{j=1}^{N} w_{j\_i} (r_{j\_i})^2 = \sum_{j=1}^{N} w_{j\_i} \left( y_j - \frac{A_i e^{-B_i x_{j\_i}}}{\sqrt{x_{j\_i}}} \right)^2 \quad (16)$$

and the residual $r_{j\_i}$ for the $j^{th}$ sensor and the $i^{th}$ potential hypocenter location is given by:

$$r_{j\_i} = y_j - \frac{A_i e^{-B_i x_{j\_i}}}{\sqrt{x_{j\_i}}} \quad (17)$$

Equation (15) may be linearized by taking the natural logarithm of both sides to obtain:

$$\ln(y_{j\_i}) = \ln(A_i) - B_i x_{j\_i} - \tfrac{1}{2}\ln(x_{j\_i}) = y'_{j\_i} = A'_i - B_i x_{j\_i} - \tfrac{1}{2}\ln(x_{j\_i}) \quad (18)$$

where $y'_{j\_i} = \ln(y_{j\_i})$ and $A'_i = \ln(A_i)$. When the assumption is made that $B_i \approx B_0$, equations (9a) and (16) may be used to solve for $A_i$ according to:

$$A_i = \frac{\sum_{j=1}^{N} w_{j\_i} y_j \frac{e^{-B_0 x_{j\_i}}}{\sqrt{x_{j\_i}}}}{\sum_{j=1}^{N} w_{j\_i} \frac{e^{-2B_0 x_{j\_i}}}{x_{j\_i}}} \quad (19)$$

The variables used in the model of equations (14)-(19) may have substantially the same meaning as those used in the above described model based on equations (6)-(11). Method 400 using the model set out in equations (14)-(19) may be similar to method 400 described above using the model of equations (6)-(11). More particularly, block 430 may involve determining the model parameters $A_i$ and $B_i$ for the $i^{th}$ potential hypocenter, block 435 may involve determining an error metric associated with the $i^{th}$ potential hypocenter (e.g. using equations (12) and (13), except that the equation (15) regression model is used in the place of the equation (7) regression model) and the remainder of method 400 may be substantially similar to that described above.

As discussed above, method 400 (FIG. 7C) represents one possible embodiment of block 270 of method 200 (FIG. 7A). The block 445 estimated hypocenter location may be the output of the block 270 event location estimation. In other embodiments, block 270 may be implemented by other methods. Returning to FIG. 7A, at the conclusion of block 270 (e.g. method 400), method 200 may proceed to optional block 275 which involves estimating an event energy. The optional block 275 energy estimation may also be based on the spatial attenuation model used in block 270 to estimate the rock fall hypocenter. In the particular exemplary embodiment described in method 400 above, the spatial attenuation model is represented by equations (6) and (7).

If it is assumed that the trajectory associated with a falling rock is predominantly vertical, then the rock's kinetic energy may be expressed as:

$$KE = mhg \qquad (14)$$

where: m is the mass of the rock, h is the height from which the rock falls and g is the acceleration due to gravity. The block 275 energy estimation may also involve the assumption that the PPV of a rock fall event at the hypocenter is proportional to the kinetic energy KE:

$$KE = kA \qquad (15)$$

where: A is the value of the model parameter $A_i$ determined in block 430 and associated with the hypocenter selected in block 445 and k is a constant of proportionality which may be determined experimentally during calibration of system 10. The block determination of the energy associated with a rock fall event may be determined using equation (15).

Figures 7D, 10:
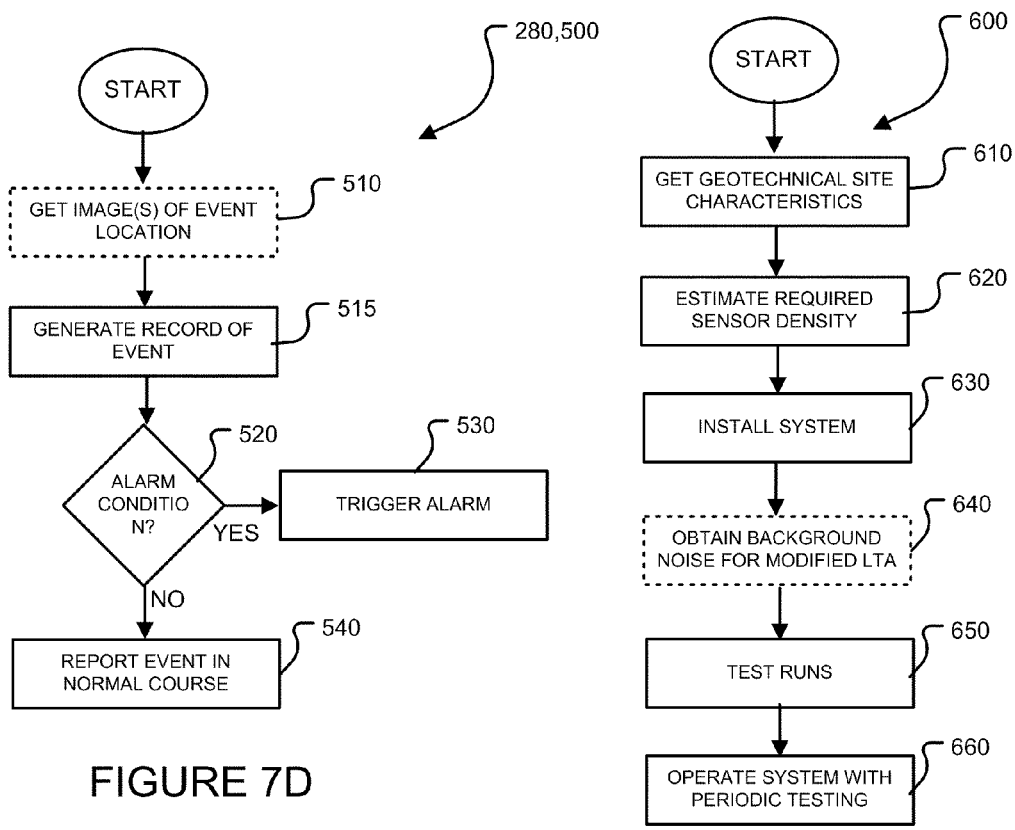
FIG. 7D schematically depicts a method for taking appropriate action in respect of a rock fall event which may be performed as a part of the FIG. 7A event detection method according to a particular embodiment.
FIG. 10 schematically illustrates a method for deployment of the FIG. 1 system according to an example embodiment.

Method 200 (FIG. 7A) proceeds to block 280 which involves taking the appropriate action for a rock fall event. FIG. 7D schematically illustrates a method 500 for taking appropriate action in respect of a rock fall event which may be performed in block 280 according to a particular embodiment. Method 500 commences in optional block 510 which involves obtaining one or more images of the estimated event location. The estimated event location may be the event location determined in block 270 (e.g. the block 445 hypocenter). Optional block 510 may involve controlling one or more image capturing devices 34 using camera control signals 38. Image capturing device(s) 34 may be controlled, so as to direct them toward the estimated event location and to capture corresponding image data 36. As discussed above, image data 36 may be stored in image data memory 130.

Method 500 then proceeds to block 515 which involves generating a record of the rock fall event. The record of the rock fall event may include recordal of a number of parameters associated with the rock fall event. In particular embodiments, the block 515 record may include one or more of: the event type (e.g. a block 395 or block 390 rock fall event); a number of triggered sensors; a number N of block 410 sensors; start and end times of the event which may include the start time ($t_{start}$) for the first triggered sensor and the end time ($t_{end}$) for the last sensor to remain triggered; the estimated location of the hypocenter of the event (e.g. the block 445 hypocenter); the estimated PPV of the event at the hypocenter (e.g. the value of the model parameter $A_i$ determined in block 430 for the hypocenter selected in block 445); the estimated event energy (e.g. the block 275 energy); the PPV and the associated time $t_{PPV}$ for each triggered sensor; the maxima (and associated times) of one or more other block 305 event specific parameters (e.g. STA/LTA$_{max}$, E$_{max}$ or the like); and any other parameter of which data processor 120 may be aware. In some embodiments, the block 515 record may also include one or more of the block 510 images of the estimated event location.

Method 500 then proceeds to block 520 which involves evaluation of an alarm criteria. In one particular embodiment, the block 520 alarm criteria may involve comparison to determine whether the estimated PPV of the event at the hypocenter (e.g. the value of the model parameter $A_i$ determined in block 430 for the hypocenter selected in block 445) is greater than a PPV alarm threshold (thresh_PPV_alarm). In other embodiments, the block 520 alarm criteria may involve comparison to determine whether the estimated event energy (e.g. the block 275 energy) is greater than an energy alarm threshold (thresh_KE_alarm). It will be appreciated, based on equation (15) above, that in the above-described embodiment, these two block 520 alarm criteria are equivalent and related by the experimentally determined scaling factor k. In some embodiments, the block 520 alarm criteria may be additionally or alternatively based on inquiries into one or more other parameter(s) measured or estimated by system 10.

If the block 520 inquiry is positive (e.g. the estimated PPV of the event at the hypocenter is greater than a PPV alarm threshold (thresh_PPV_alarm)), then method 500 proceeds along the block 520 YES output to block 530 which may involve triggering an alarm and/or transmitting the block 515 event record directly back to an offsite location (e.g. via network connection 28 to remote workstation 30). The block 530 alarm may involve triggering sensory stimulus at remote workstation 30 and/or an email at remote workstation 30 or the like. In some embodiments, when the block 530 alarm is received at remote workstation 30, the block 515 event record (including any block 510 images) may be evaluated by human personnel. If the event is determined by human personnel to be worthy of service disruption, then vehicular traffic may be prevented from traveling on track section 12 until the event is investigated more thoroughly and/or cleared. In some embodiments, human intervention may not be desired or required and the block 530 alarm may cause a communication to be directed to rail vehicle operators to alert them to the event and to cause them to stop traveling on or toward track section 12.

If the block 520 inquiry is negative (e.g. the estimated PPV of the event at the hypocenter is less than the PPV alarm threshold (thresh_PPV_alarm)), then method 500 proceeds along the block 520 NO output to block 540. In the illustrated embodiment, block 540 involves transmitting and/or logging the event in the normal course (i.e. without triggering an alarm). Block 540 may involve storing the block 515 event record in local memory (e.g. in data logger 110, memory 128 and/or image data memory 130) until such time as signal processing unit 26 is polled for events (e.g. by remote workstation 30 over network connection 28). Depending on the availability of local memory, in other embodiments, block 540 may involve transmitting the block 515 event record (e.g. to remote workstation 30 over network connection 28) without triggering an alarm.

FIG. 10 schematically illustrates a method 600 for deployment of system 10 according to an example embodiment. Method 600 commences in block 610 which involves assessing geotechnical characteristics of the environment in the vicinity of track section 12. Block 610 may involve simulating rock fall events using drops of known weights from known heights at known locations (i.e. test drops). Block 610 may involve using portable sensor arrays (similar to sensor arrays 18) and portable signal processing units 26. Block 610 may involve assessing one or more of:

ambient noise characteristics (including, by way of non-limiting example, characterizing noise from sources such as waterfalls, running water sources, winds, nearby traffic and other sources of surface noise);

the surface wave velocity in the substrate in a vicinity of track section 12;

the soil quality factor (e.g. the parameter $B_0$ described above);

the accuracy range of block 270 location estimation method (e.g. the inventors have determined that the accuracy of method 400 may decrease with distance between the sensors and the rock fall location);

assessing an amount of data scattering resulting from acoustic energy crossing an obstacle (e.g. the track in circumstances where sensors are installed on both sides of track section 12 or if track section 12 has curvature) and, if significant energy loss takes place, then determining that data from "shadowed" sensors should not be mixed with the remaining sensors;

verifying that gain settings associated with signal conditioning circuitry 102 are suitable to capture events in a range of interest; and/or the like.

Method 600 then proceeds to block 620 which involves using the block 610 information to determine a sensor density for system 10 and determining the associated system layout. Block 620 may involve comparing PPVs associated with test drops at various distances against background noise. In some embodiments, the PPV of the smallest event necessary to be detected should be greater than 3 times the background noise level. In other embodiments, this ratio is 4-5 times.

Method 600 then proceeds to block 630 which involves installing system 10 in accordance with the block 620 layout. The portable sensor arrays and portable signal processing units may be replaced by permanent sensor arrays 18 and signal processing unit 26. Some of the geotechnical parameters determined in block 610 may be reassessed using the permanent system components. Optional block 640 may involve determining a background noise level (and an associated LTA constant c) which may be used, in some embodiments, to compute the modified STA/LTA ratio in accordance with equation (3) described above.

Method 600 then proceeds to block 650 which involves testing system 10 by running system 10 for a period of time sufficient to capture all types of detectable events. System 10 (and in particular software 124 used by data processor 120) may be adjusted as needed during this testing period to optimize performance. Digital sensor signals associated with particular events may be recorded so that they can be used again to evaluate changes to software 124. In block 660, system 10 is commissioned to operate, but is subject to regular routine testing and recalibration as desired.

Figure 11:
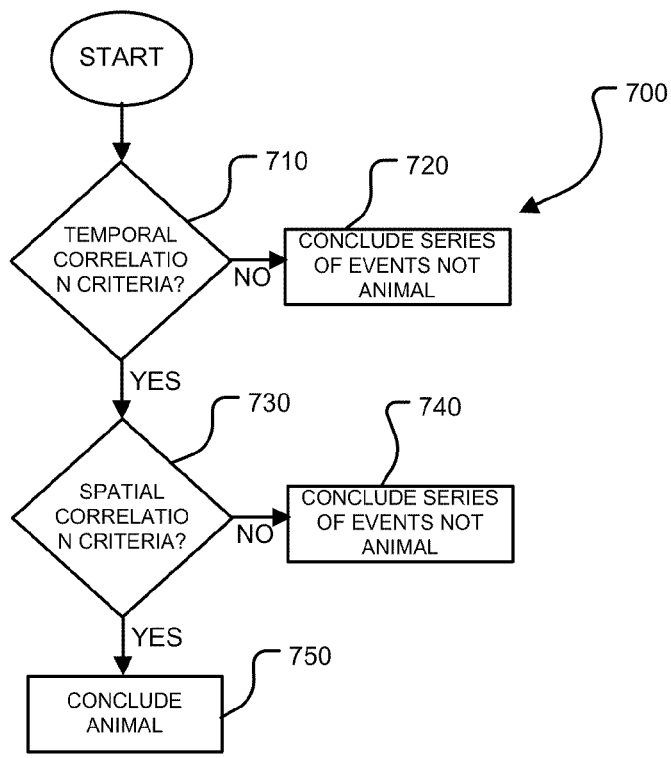
FIG. 11 schematically illustrates a method for discriminating a series of events that may be caused by a human or other animal according to a particular embodiment.

In some embodiments, it may be desirable to attempt to discriminate events (and/or series of events) caused by human(s) and/or other animal(s) from events caused by rock fall, rail traffic and/or other source of surface noise. FIG. 11 illustrated a method 700 which may be used to discriminate a series of events that may be caused by a human or other animal according to a particular embodiment. Method 700 may be performed in method 200 (FIG. 7A) after the detection of an event. For example, method 700 may be performed between blocks 260 and 265 and/or between blocks 275 and 280.

Method 700 commences in block 710 which involves determining a temporal correlation between the current event and the previous M events. The parameter M may be based on empirical evidence and may depend on sensor sensitivity, the importance of detection of animals in the vicinity of track section 12 or the like. The block 710 temporal correlation may be determined using a wide variety of techniques known to those skilled in the art. One such technique involves determining a mean time of the last M events (e.g. the mean start time $t_{start}$ of the last M events) and comparing the time that is furthest from the mean time with the mean time. In accordance with this technique, a large difference indicates a fairly weak temporal correlation and a small difference indicates a fairly strong temporal correlation. Another technique involves computing the statistical standard deviation σ of the times of the last M events (e.g. the mean start times $t_{start}$ of the last M events). In accordance with this technique, a large deviation indicates a relatively weak temporal correlation, whereas a small deviation indicates a relatively strong temporal correlation.

If the block 710 inquiry indicates that the temporal correlation of the last M events is less than a threshold (temp_corr_thresh), then method 700 may proceed along the block 710 NO output to block 720 where method 700 concludes that the series of events were not produced by an animal. If, on the other hand, the block 710 inquiry indicates that the temporal correlation of the last M events is greater than a threshold (temp_corr_thresh), then method 700 may proceed along the block 710 YES output to block 730. Block 730 involves evaluation of a spatial correlation of the last N events. In some embodiments, the block 710 number of events M is equal to the block 730 number of events N. The block 730 spatial correlation may be determined on the basis of the event locations determined in block 270 (e.g. method 400), for example. The block 730 spatial correlations may be determined using any of a large variety of techniques known to those skilled in the art, including those described above for block 710.

If the block 730 inquiry indicates that the spatial correlation of the last N events is less than a threshold (spat_corr_thresh), then method 700 may proceed along the block 730 NO output to block 740 where method 700 concludes that the series of events were not produced by an animal. If, on the other hand, the block 730 inquiry indicates that the spatial correlation of the last N events is greater than a threshold (spat_corr_thresh), then method 700 may proceed along the block 730 YES output to block 750, which involves concluding that the series of events was most likely caused by human(s) or other animal(s).

Where track section 12 is located in a region having relatively large amounts of active train traffic and/or highrail vehicular traffic, there is a relatively high likelihood of false positive events related to such active train and/or highrail vehicular traffic. In addition to trains and highrail vehicles that are moving at regular speed through such active regions, such active regions may be associated with relatively large amounts of "cultural noise". Such cultural noise may include, by way of non-limiting example, slow or stationary trains or highrail vehicles, movement of track maintenance personnel and/or equipment, site excavation and/or construction work and the associated movement of personnel and/or equipment, right-of-way maintenance and/or the like. In such active regions (or in any other regions), it may be desirable to include additional sensors, additional processing techniques and/or other additional techniques to minimize (to the extent possible) the detection of false positive events.

In some embodiments, system 10 may include particular vehicle detection sensors for detecting slow moving and/or stationary trains, slow moving and/or stationary highrail vehicles and/or other vehicles operating in a vicinity of such active track sections. Such vehicle detection sensors may include, for example, magnetometers which may be mounted directly to track section 12 and/or at a distance (e.g. 0.5 m-2.5 m) away from track section 12 (e.g. in ballast 52), ultrasound vehicle sensors, optical (e.g. infrared) vehicle sensors and/or the like. Magnetometers may sense the presence of iron or other magnetic materials associated with trains and/or highrail vehicles. Ultrasound vehicle sensors may sense the presence of trains and/or highrail vehicles using reflected acoustic energy. Optical vehicle sensors may sense the presence of trains and/or highrail vehicles by sensing the interruption of an optical (e.g. infrared) beam.

Vehicle detection sensors which may be incorporated into system 10 to detect slow moving and/or stationary trains, slow moving and/or stationary highrail vehicles and/or other vehicles operating in a vicinity of track section 12 may additionally or alternatively include magnetic wheel detectors of the type used in the rail industry to trigger so-called "hot box" detectors. Such wheel detectors may be mounted directly to track section 12 (e.g. tracks 54 and/or ties 56). As their name implies, magnetic wheel detectors may be used to detect the wheels of trains and highrail vehicles.

Figure 12A:
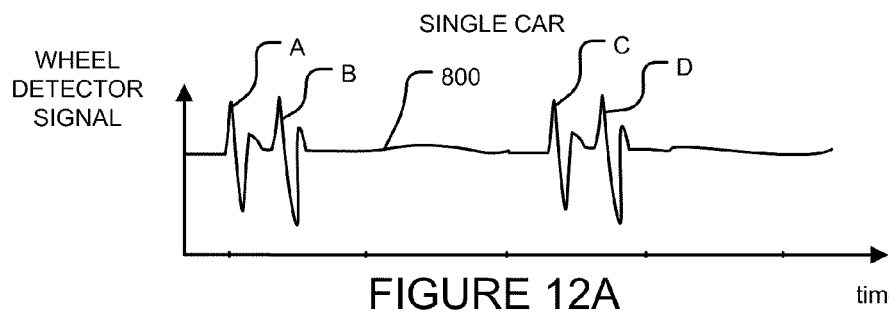
FIG. 12A schematically depicts a typical signal associated with the passage of a typical train car over a magnetic wheel detector.

A typical rail car may have a total of eight wheels (four on each side) with four (two on each side) near the front of the car and four (two on each side) near the rear of the car. FIG. 12A schematically depicts a typical signal 800 emitted from a magnetic wheel detector in response to the passage of a single car of a train over the wheel detector (after suitable amplification and optional temporal filtering (e.g. smoothing to reduce high frequency noise)). It can be seen from FIG. 12A that signal 800 exhibits four spikes A, B, C, D. Spikes A, B, C, D correspond to the detection of the four rail car wheels (on one side of the car) by the wheel detector magnet. The first two spikes A, B of signal 800 are associated with the two wheels near the front of the car and the second two spikes C, D are associated with the two wheels near the rear of the car (assuming that the car is moving forwardly).

Figure 12B:
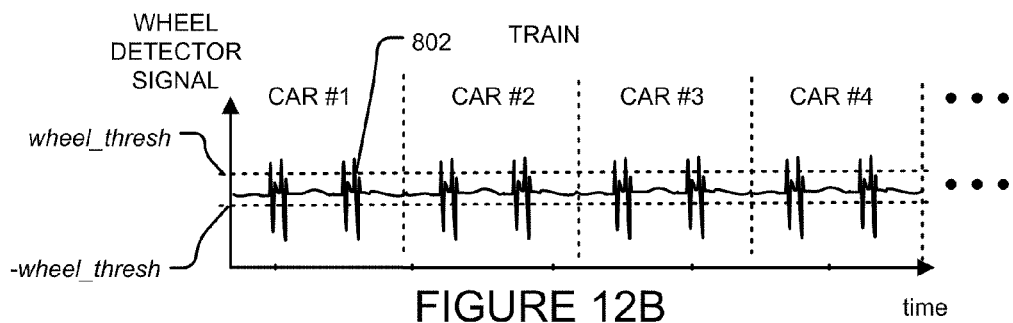
FIG. 12B schematically depicts a typical signal associated with the passage of a typical multi-car train over a magnetic wheel detector.

The wheel detector signal for a highrail vehicle (having the same wheel pattern as the rail car associated with the FIG. 12A signal) may exhibit a shape similar to that of signal 800, except that the time between the first two spikes and the second two spikes may be less because of the relatively short distance between the front wheels and rear wheels of a highrail vehicle. For train cars or highrail vehicles with different wheel patterns, signal 800 may have a different signature. However, there will typically be an identifiable signal feature (e.g. a spike or the like) associated with each wheel (on one side) of the car/vehicle. FIG. 12B schematically shows a typical signal 802 emitted from a magnetic wheel detector in response to the passage of a train having multiple cars (after suitable amplification and optional temporal filtering (e.g. smoothing to reduce high frequency noise)). It can be seen from signal 802 that a feature pattern or signature similar to that of signal 800 (FIG. 12A) is repeated for each car in the train.

In some embodiments, system 10 may comprise one or more vehicle detection sensors (e.g. magnetometers, ultrasound vehicle sensors, optical vehicle sensors, wheel detectors and/or the like) which may be used to detect the presence of a train or a highrail vehicle on track section 12 and/or to discriminate whether a detected/triggered event is a train or highrail vehicle on track section 12. Such vehicle detection sensors may be provided as part of one or more corresponding sensor arrays 18 and may provide corresponding vehicle detection information 22 to signal processing unit 26 over transmission lines 24. Alternatively, such vehicle detection sensors could be provided independently of sensor arrays 18 and may independently communicate with signal processing unit 26. Vehicle detection information received from vehicle detection sensors may be handled by signal processing unit 26, DAU 116 and/or data logger 110 in the same or similar manner as other sensor information 22 discussed herein. Data from vehicle detection sensors may be logged during a time period when an event is triggered (e.g. between the times of a block 225 YES output and a block 245 YES output (FIG. 7A)) or may be logged continually. Once stored in data logger 110 or DAU 116, information from vehicle detection sensors can be processed by data processor 120 to generate other forms of processing parameters 150. Some or all of these processing parameters 150 may be used in turn to detect the presence of a train or a highrail vehicle on track section 12 and/or to discriminate whether a detected/triggered event is a train or highrail vehicle on track section 12 (e.g. as a part of block 255 and/or method 300).

A number of exemplary embodiments incorporating wheel detector type vehicle sensors are now described. It will be appreciated that in many instances, other types of vehicle detection sensors could be used in addition to, or as alternatives to, wheel detectors with suitably appropriate modifications of the exemplary embodiments described herein.

Signals from one or more wheel detectors may be subjected to an amplitude thresholding criteria to detect the presence of a train or a high rail vehicle on track section 12. Referring to FIG. 12B, if it is determined that the absolute value of a wheel detector signal is greater than a threshold value wheel_thresh, then it may be concluded that there is a train or highrail vehicle overtop of the wheel detector at that time or that a triggered event was the result of a train or highrail vehicle. In some embodiments, system 10 may record or otherwise observe a time associated with each instance that the wheel detector signal crosses the threshold wheel_thresh. In some embodiments, system 10 may record or otherwise observe only times associated with the absolute value of the wheel detector signal crossing the threshold wheel_thresh in a particular direction (e.g. from below the threshold to above the threshold or vice versa). In some embodiments, the value of wheel_thresh may be low or even zero, since a typical wheel detector is not particularly noisy or susceptible to false positive events.

Such a thresholding criteria may be incorporated into the post event processing of block 255 and/or method 300 described above. For example, if it is determined that the absolute value of a wheel detector signal was greater than the threshold wheel_thresh at any time during the event period (e.g. between $t_{start}$ and $t_{end}$), then block 255/method 300 may conclude that the event was a train or high rail vehicle. As another example, if it is determined that the absolute value of a wheel detector was greater than the threshold wheel_thresh a number of times during the event period (e.g. between $t_{start}$ and $t_{end}$), but that this number of times was less than a threshold number of times wheel_num_thresh, then block 255/method 300 may conclude that the event was a highrail vehicle as opposed to a train.

Figure 12C:
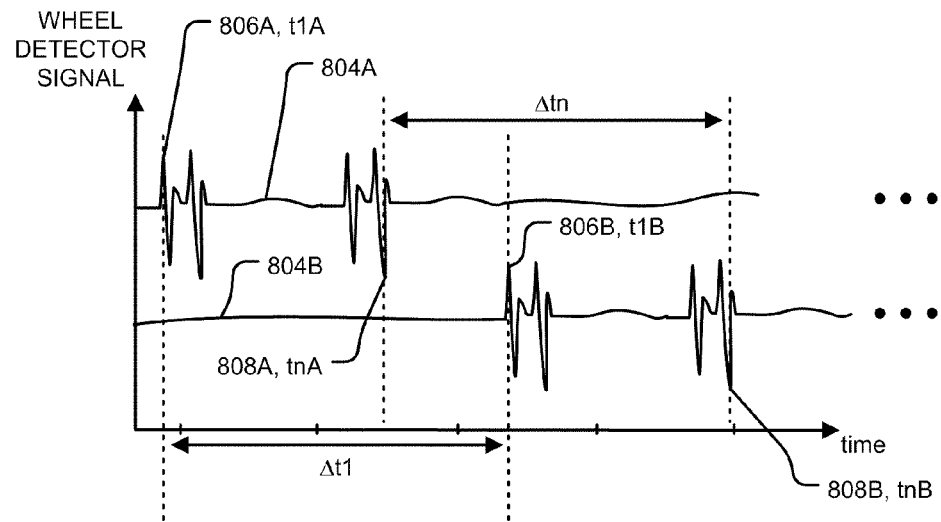
FIG. 12C schematically depicts the extraction of temporal differences between corresponding features of the signals associated with a pair of wheel detectors.

In addition to detecting the presence of a highrail vehicle or train, system 10 may use a plurality of wheel detectors spaced apart from one another by known distances to estimate the direction and/or speed of a passing vehicle. For example, where two wheel detectors are spaced apart from one another by a known distance D, the direction of travel of the passing vehicle may be determined by detecting which wheel detector signal leads the other and an estimate of the speed of the train or the highrail vehicle may be determined by dividing the wheel detector separation distance D by the temporal difference between corresponding features of the wheel detector signals at the two wheel detectors. FIG. 12C schematically depicts wheel detector signals 804A, 804B associated with the passage of a highrail vehicle over a pair of wheel detectors and the manner in which temporal differences between corresponding features of wheel detector signals 804A, 804B may be used to determine the direction and speed of a vehicle. It can be seen from FIG. 12C, that signal 804A leads signal 804B. System 10 may therefore determine that the train or highrail vehicle that generated signals 804A, 804B was moving from the direction of the sensor associated with signal 804A toward the direction of the sensor associated with signal 804B. FIG. 12C exhibits a temporal difference $\Delta t_1$ between corresponding spikes 806A, 806B of wheel detector signals 804A, 804B. The speed of a train or highrail vehicle may be estimated to be $$v_1 = \frac{D}{\Delta t_1} = \frac{D}{(t_{1B} - t_{1A})},$$

where $t_{1A}$ may be the time that signal 804A crosses the threshold wheel_thresh at peak 806A and $t_{1B}$ may be the time that signal 804B crosses the threshold wheel_thresh at peak 806B.

In addition to the first temporal difference $\Delta t_1$ between corresponding first spikes 806A, 806B of wheel detector signals 804A, 804B, FIG. 12C exhibits the determination of a subsequent temporal difference $\Delta t_n$ between corresponding subsequent spikes 808A, 808B of wheel detector signals 804A, 804B. System 10 may estimate the speed of a train or highrail vehicle at a subsequent time associated with the $n^{th}$ corresponding features of wheel detector signals 804A, 804B to be $$v_n = \frac{D}{\Delta t_n} = \frac{D}{(t_{nB} - t_{nA})},$$

where $t_{nA}$ may be the time that signal 804A crosses the threshold wheel_thresh at peak 808A and $t_{nB}$ may be the time that signal 804B crosses the threshold wheel_thresh at peak 808B.

In some embodiments, system 10, may estimate a speed for all corresponding features of wheel detector signals 804A, 804B (e.g. every time the absolute value of wheel detector signals 804A, 804B both cross the threshold wheel_thresh), for all corresponding features of wheel detector signals 804A, 804B when wheel detector signals 804A, 804B cross the threshold wheel_thresh in a certain direction (e.g. every time the absolute value of wheel detector signals 804A, 804B both cross from below, to above, the threshold wheel_thresh), or for every number of corresponding features of wheel detection signals 804A, 804B (e.g. every $k^{th}$ corresponding feature) of wheel detector signals 804A, 804B. The number k of features between speed estimates can be a configurable parameter of system 10 and may depend on available processor resources. In some embodiments, data from wheel detectors may be logged and corresponding speeds may be estimated only after an event has been triggered (e.g. after the block 225 inquiry results in a YES output (FIG. 7A) or after $t_{start}$). The correspondence between features of the signals 804A, 804B associated with a pair of wheel detectors may be maintained by suitable indices which may be incremented each time that a threshold crossing event (e.g. a wheel detection signal 804A, 804B crosses wheel_thresh) is recorded for that wheel detection signal 804A, 804B.

In some embodiments, the estimated speeds $v_n$ (or the determined temporal differences $\Delta t_n$) at different times may be processed (e.g. integrated or differentiated) to determine an estimated position and/or acceleration/deceleration of a train or highrail vehicle. Such information may be used to estimate the location that a train or highrail vehicle comes to rest on track section 12. Some systems may incorporate more than two wheel detectors. In such systems, velocity, position and/or acceleration estimates based on different sensor pairs can be combined (e.g. averaged) to determine a better estimate of the vehicle velocity, position and/or acceleration. Also, velocity differences between different sensor pairs could be used as another technique for estimating acceleration. For example, if sensor A is spaced apart from sensor B by a distance D and sensor B is spaced apart from sensor C by a distance D, and it is determined that the temporal difference $\Delta t_{AB}$ between the sensor A and B signals for a particular feature is greater than the temporal difference $\Delta t_{BC}$ between the sensor B and C signals for the same particular feature, then it may be concluded that the vehicle is accelerating as it moves from sensor A to B to C.

In some embodiments, system 10 may detect the presence of trains and/or highrail vehicles on track section 12 using the cross-correlation of signals from multiple sensors of the same type which are spaced apart from one another by known distances D. Sensors which may be used for this cross-correlation process may include ballast sensors (e.g. acoustic ballast sensors 50 of the type described above), rail sensors (e.g. rail sensors 80 of the type described above), wheel detectors and/or the like. Cross-correlation data may be generated for time periods when an event is triggered (e.g. between the times of a block 225 YES output and a block 245 YES output (FIG. 7A)) or may be logged continually. Once obtained, cross-correlation data can be processed by data processor 120 to generate other forms of processing parameters 150. Some or all of these processing parameters 150 may be used in turn to detect the presence of a train or a highrail vehicle on track section 12 and/or to discriminate whether a detected/triggered event is a train or highrail vehicle on track section 12 (e.g. as a part of block 255 and/or method 300).

Figure 13:
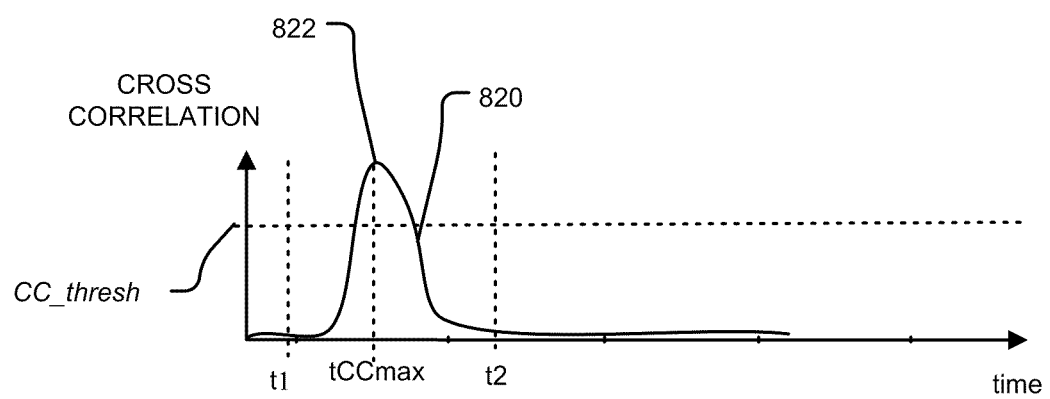
FIG. 13 exhibits a typical cross-correlation waveform associated with signals from a pair of spaced apart ballast sensors when a train is moving (or has moved) over the FIG. 1 track section at a relatively constant speed.

FIG. 13 exhibits a typical cross-correlation waveform 820 associated with the signals from a pair of spaced apart ballast sensors 50 when a train is moving (or has moved) over track section 12 at a relatively constant speed (after suitable amplification and optional temporal filtering (e.g. smoothing to reduce high frequency noise) of the signals from sensors 50). It can be seen from FIG. 13, that cross-correlation waveform 820 exhibits a reasonably sharp peak 822 at a time $t_{CCmax}$.

In some embodiments, system 10 may determine the presence of a train or a highrail vehicle on track section 10 when peak 822 of cross-correlation waveform 829 is greater than a threshold value CC_thresh and when the absolute value of the time $t_{CCmax}$ of peak 822 occurs within a window between the times $t_1$ and $t_2$. This determination may be a part of block 255/method 300, although this is not necessary. The threshold CC_thresh may be experimentally determined and may be a configurable parameter of system 10. In some embodiments, the times $t_1$ and $t_2$ can be configured to correspond to maximum and minimum expected speeds of a train or highrail vehicle. For example, if a train is expected to move with a maximum speed $v_{max}$ and it is known that the sensors associated with cross-correlation signal 820 as spaced from one another by a distance D, then $t_1$ may be set to $$t_1 = \frac{D}{v_{max}}$$

and the train is expected to move with a minimum speed $v_{min}$, then $t_2$ may be set to $$t_2 = \frac{D}{v_{min}}.$$

The times $t_1$, $t_2$ can also be experimentally determined and configured parameters of system 10. The actual speed of a train or highrail vehicle may be estimated from the time $t_{CCmax}$ associated with the peak 822 of cross-correlation signal 820 according to $$v = \frac{D}{t_{CCmax}}.$$

This variation of this speed estimate over time may be processed (e.g. integrated or differentiated) to determine an estimated position and/or acceleration/deceleration of a train or highrail vehicle. Such information may be used to estimate the location that a train or highrail vehicle comes to rest on a track section 12. The direction of travel of a train or highrail vehicle can also be determined from the cross-correlation between two sensors, since the time $t_{CCmax}$ associated with the cross-correlation peak 822 will be in the positive or negative half axis depending on the direction of motion of the train or highrail vehicle.

In some embodiments, cross-correlation analysis may be performed on a plurality of different sensor combinations (e.g. combinations involving more than two sensors) before concluding that an event is associated with a train or highrail vehicle (i.e. that an event is not a rock fall). For example, it may be required that each (or some percentage) of the cross-correlations of a plurality of different sensor combinations exhibits a peak that is greater than a threshold CC_thresh and occurs within a specified temporal window before concluding that an event is a train or a highrail vehicle. The cross-correlation of two or more different sensor combinations can also be used to estimate the acceleration of a vehicle. Consider again the example where sensor A is spaced apart from sensor B by a distance D and sensor B is spaced apart from sensor C by a distance D. If the time of the cross-correlation peak ($t_{CCmax}$) is greater for the cross-correlation of the signals from sensors A and B than the time of the cross-correlation peak ($t_{CCmax}$) for the cross-correlation of the signals from sensors B and C, then it can be concluded that the train/vehicle is accelerating as it moves from A to B to C. As another example, if the time of the cross-correlation peak ($t_{CCmax}$) for the signals from sensors A and C is less than twice the time of the cross-correlation peak ($t_{CCmax}$) for the signals from sensors A and B, then it can be concluded that the train/vehicle is accelerating as it moves from A to B to C.

In some embodiments, system 10 may include the ability for all or part of system 10 to be temporarily shut-off in some circumstances. For example, a signal may be sent to signal processing unit 26 via network connection 28 (or otherwise communicated to system 10) which causes system 10 (e.g. signal processing unit 26) to temporarily disable (e.g. disregard information received from) one or more of sensor arrays 18. This temporary shut-off signal may be generated in any of a variety of manners. By way of non-limiting example, if track maintenance, right-of-way, excavation or construction personnel and/or equipment will be working in a vicinity of a particular group of sensor arrays 18, then:

- a shut-off signal for that group of sensor arrays 18 may be communicated from a communication device (not shown) connected to network connection 28 by such personnel (or by other suitable personnel);
- optional cameras 34 may be motion activated and may communicate video signal(s) (e.g. via network connection 28) to a person who may determine whether a group of sensors arrays 18 should be temporarily shut-off;
- a signal may be communicated to system 10 from a GPS-enabled device carried by such personnel or coupled to such equipment which may indicate the location of the personnel or equipment and may thereby enable system 10 to determine which sensor arrays 18 should be temporarily disabled; and/or
- a signal from some other sensor or group of sensors (e.g. a light-activated IR sensor, a radio frequency identification (RFID) sensor and/or the like) may be communicated to system 10. Such sensors may be strategically located to indicated to system 10 which sensor arrays 18 should be temporarily disabled.

In cases where system 10 is shut-off in whole or in part by way of a manually generated signal, then it may be desirable to have some automated technique for re-activating system 10 to avoid such personnel accidentally leaving system 10 in a shut-off state. By way of non-limiting example, such automated technique may include: a temporal re-activation (e.g. system 10 reactivates after a period (e.g. a user configurable period) of time; a sensor based reactivation (e.g. system 10 reactivates when a light sensor determines that it is dark, where a GPS-enabled device determines that it is outside of a vicinity of track section 12 or the like); an automated reminder to a suitable person to reactivate system 10 (e.g. communicated over network 28); and/or the like.

As will be apparent to those skilled in the art in the light of the foregoing disclosure, many alterations and modifications are possible in the practice of this invention without departing from the spirit or scope thereof. For example:

- The particular embodiments of the methods described above are exemplary in nature. In other embodiments, portions of these methods my be modified or changed. In some embodiments, aspects of these methods may be performed in suitable orders other than the orders described above. By way of non-limiting example, in some embodiments of method 300 (FIG. 7B), the procedures of blocks 360-390 may be performed before the procedures of blocks 310-330 and/or blocks 335-355 or the procedures of blocks 335-355 may be performed prior to the procedures of blocks 310-330. Those skilled in the art will appreciate that there are other circumstances in which the order of particular operations may be changed in circumstances where this is desirable.
- Method 300 of the illustrated embodiment described above involves discriminating a variety of different types of events (i.e. train events, highrail vehicle events, surface noise events, insignificant rock fall events and significant rock fall events. This is not necessary. In some embodiments, it is desirable to discriminate a smaller number of events (e.g. the two categories of significant rock fall events and other events). In such embodiments, method 300 may be suitable modified such that the block 310 NO output, optional block 335 YES output, block 360 NO output and block 392 YES output all lead to the same conclusion (i.e. other type of event) and method 300 may conclude a significant rock fall event when the block 392 inquiry is negative (i.e. block 392 NO output). In other such embodiments, some of blocks 365-390 may be maintained to discriminate small rock fall events or rock fall accumulation.
- In some embodiments, method 200 and/or method 300 may be modified to provide an inquiry into a minimum delay between events (Δevent). Events which occur at within a time (and/or number of samples) separation less than the minimum delay Δevent from one another may be determined to belong to the same event. In particular embodiments, such closely spaced events may be merged into a single event or one or more of such closely spaced events may be ignored.

In some embodiments, method 200 and/or method 300 may be modified to provide an inquiry into a minimum number of triggered sensors (#_sensor_min). If the number of sensors triggered by an even is less than this minimum number of sensors (#_sensor_min), then the event can be determined to be too small to be of concern.

FIG. 9B described above makes use of a parameter $\Delta T_{start}$ to determine the sensors to be included in the block 410 group of sensors. This parameter $\Delta t_{start}$ or a similar (possibly larger) temporal parameter may be used to determine a maximum arrival time difference. If a first sensor is triggered at a time $t_{start\_sensor\#1}$ and one or more sensors become triggered after this maximum arrival time difference, then the subsequently triggered sensors can be determined to belong to a separate event. The maximum arrival time difference can be determined based at least in part of the experimentally determined surface wave velocity in the substrate in a vicinity of track section 12.

Some of the above described embodiments describe using an experimentally determined average $B_0$ for the model parameter $B_i$ of equation (7) and/or equation (15). In some embodiments, this parameter $B_0$ may be the same for a particular track section 12, but may differ as between each of a plurality of modular track sections 12 which may be incorporated into a overall system or this parameter $B_0$ may vary locally within a track section (12).

The methods described above involve the discrimination of a number of events. These events represent non-limiting examples of events that may be discriminated by system 10. In other embodiments, system 10 may be configured to discriminate other types of events, such as, by way of non-limiting example: switch points being moved, locomotive bells/horns and thermal expansion and the accompanying rail creep atop the ties caused by solar heating of the rail.

In some embodiments, system 10 can exhibit one of two states—rock fall and clear-to-pass. The rock fall state can indicate that system 10 has detected an event that may be a rock fall and consequently a train should not pass through track section 12 without taking precautionary measures (e.g. slowing to a speed at which braking may be effective, stopping and waiting for a crew to arrive to investigate the event, stopping and waiting for the state of system 10 to enter the clear-to-pass state and/or the like. To be as safe as possible, system 10 may default to the rock fall state. System 10 can raise and alarm or take other suitable action when it determines that its state should be changed to rock fall. In some embodiments, system 10 can be reset from a rock fall state to a clear-to-pass state if a train passes through track section 12 without incident. For example, if system 10 is in a rock fall state, then a precautionary measure that could be taken is for a train to slow to a speed where the train could be safely brought to a stop after visually sighting a rock fall event. If, however, the train is able to pass through the site of the predicted rock fall event without incident, then the state of system 10 may be reset to clear-to-pass.

In some embodiments (e.g. applications where the reliability of system 10 is considered to be crucial), system 10 may be made redundant through use of redundant components. For example, referring to FIG. 1, system 10 may be modified to include redundant sensors arrays 18 (e.g. each individual sensor array 18 shown in FIG. 1 would be replaced by a plurality of redundant sensors arrays 18, if one sensor array 18 were to fail, system 10 could revert to its redundant backup sensor array). By way of non-limiting example, system 10 could also comprise redundant image capture devices 34, transmission lines 24, signal processing units 26 and network connections 28.

Optional image capturing devices (e.g. cameras) 34 may be remotely controlled by a user via network connection 28. In some embodiments, upon detection of a rock fall event (or any other event) by system 10, system 10 and/or a remote user may control image capture devices 34 to capture one or more images of the event location. Images captured by image capture devices 34 may be communicated over network connection 28 to a control center, where they may be reviewed by an operator. The operator may then decide manually whether the event is a legitimate rock fall event or whether the event is some other type of event.

The term acoustic is used throughout this description and the accompanying claims. It will be appreciated that in the context of this description and the accompanying claims, the term acoustic should be understood to refer generally to mechanical and/or vibrational energy which may travel through any medium. Acoustic waves and acoustic sensors should be understood to refer generally to waves which transfer this mechanical and/or vibrational energy through any medium and sensors which detect this mechanical and/or vibrational energy.

Accordingly, the scope of the invention should be determined in accordance with the following claims.

What is claimed is:
1. A system for detection of rock fall in a vicinity of a section of railway track, the system comprising:
a plurality of ballast sensors spaced apart along the track section, each ballast sensor located in a ballast proximate to the track section but spaced apart from rails and ties associated with the track section and each ballast sensor sensitive to acoustic energy and configured to generate a corresponding ballast sensor signal in response to detecting acoustic energy;
a signal processing unit operatively connected to receive the ballast sensor signals from the plurality of ballast sensors, the signal processing unit configured to detect rock fall events in a vicinity of the track section based, at least in part, on the ballast sensor signals;
wherein the signal processing unit is configured to detect a plurality of different types of events comprising rock fall events, train events wherein a train travels over the track section and highrail vehicle events wherein a highrail vehicle travels over the track section and wherein the signal processing unit is configured to discriminate rock fall events from train events or highrail vehicle events;
wherein the signal processing unit is configured to detect an event for a particular one of the ballast sensors based, at least in part, on its corresponding ballast sensor signal;
wherein the signal processing unit is configured to detect a start of the event and an associated time $t_{start}$ for the particular one of the ballast sensors, when a STA/LTA parameter associated with the corresponding ballast sensor signal is greater than a start trigger threshold (thresh_start);

wherein the signal processing unit is configured to determine the STA/LTA parameter for the corresponding ballast sensor signal according to one of:

$$\left(\frac{STA}{LTA}\right)_n = \frac{\frac{\sum_{i=(n-(a-1))}^{i=n} |x_i|}{a}}{\frac{\sum_{i=(n-(b-1))}^{i=n} |x_i|}{b}} \quad (i)$$

where $b > a > 0$ and $n \geq a, b$ where: $x_i$ represents a value of an $i^{th}$ sample of the corresponding ballast sensor signal, n is an index of a current sample $x_n$, a is an STA duration constant, b is an LTA duration constant and $$\left(\frac{STA}{LTA}\right)_n$$

is the STA/LTA parameter; and $$\left(\frac{STA}{LTA}\right)_{mod,n} = \frac{\frac{\sum_{i=(n-(a-1))}^{i=n} x_i}{a}}{c} \quad (ii)$$

where $n > a > 0$ where: $x_i$ represents a value of an $i^{th}$ sample of the corresponding ballast sensor signal, n is an index of a current sample $x_n$, a is an STA duration constant, c is an experimentally determined constant that is representative of an LTA during event free times and $$\left(\frac{STA}{LTA}\right)_{mod,n}$$

is the STA/LTA parameter.

2. A system according to claim 1 wherein the signal processing unit is configured to detect an end of the event and an associated time $t_{end}$, for the particular one of the ballast sensors, when the STA/LTA parameter associated with the corresponding ballast sensor signal is less than an end trigger threshold (thresh_end).

3. A system according to claim 1 wherein the signal processing unit is configured to determine a duration $t_{dur}$ associated with the event for the particular one of the ballast sensors based, at least in part, on its corresponding ballast sensor signal.

4. A system according to claim 3 wherein the signal processing unit is configured to compare the event duration $t_{dur}$ with one or more duration criteria and to determine on the basis of this comparison that the event is not a rock fall event.

5. A system according to claim 4 wherein the signal processing unit is configured to determine that the event is a train event or a highrail vehicle event based at least in part on the comparison of the event duration $t_{dur}$ with the one or more duration criteria.

6. A system according to claim 5 wherein the signal processing unit is configured to determine, for the particular one of the ballast sensors, a PPV parameter which represents a magnitude of a sample of the corresponding ballast sensor signal with the largest absolute value during the event and wherein the signal processing unit is configured to compare the PPV parameter with one or more magnitude criteria and to determine on the basis of this comparison whether the event is a train event or a highrail vehicle event.

7. A system according to claim 1 wherein the signal processing unit is configured to determine a spectral power distribution associated with the event for the particular one of the ballast sensors based, at least in part, on its corresponding ballast sensor signal.

8. A system according to claim 7 wherein the signal processing unit is configured to compare the spectral power distribution with one or more spectral criteria and to determine on the basis of this comparison that the event is not a rock fall event.

9. A system according to claim 8 wherein the one or more spectral criteria comprise a frequency threshold (thresh_freq) and the signal processing unit is configured to determine that the event is a train event or a highrail vehicle event when the spectral power distribution comprises more than a particular percentage of its power at frequencies above the frequency threshold (thresh_freq).

10. A system according to claim 9 wherein the signal processing unit is configured to determine, for the particular one of the ballast sensors, a PPV parameter which represents a magnitude of a sample of the corresponding ballast sensor signal with the largest absolute value during the event and the signal processing unit is configured to compare the PPV parameter with one or more magnitude criteria and to determine on the basis of this comparison whether the event is a train event or a highrail vehicle event.

11. A system according to claim 1 comprising one or more rail sensors, each rail sensor operatively contacting the rails or the ties associated with the track section and each rail sensor sensitive to acoustic energy and configured to generate a corresponding rail sensor signal in response to detecting acoustic energy and wherein the signal processing unit is operatively connected to receive the rail sensor signal.

12. A system according to claim 11 wherein the signal processing unit is configured to determine a rail sensor spectral power distribution associated with the event for a particular one of the rail sensors based, at least in part, on its corresponding rail sensor signal and configured to compare the rail sensor spectral power distribution with one or more spectral criteria and to determine on the basis of this comparison that the event is not a rock fall event.

13. A system according to claim 1 wherein the signal processing unit is configured to determine a PPV parameter associated with the event for the particular one of the ballast sensors and its corresponding ballast sensor signal, the PPV parameter representing a magnitude of a sample of the corresponding ballast sensor signal with the largest absolute value during the event.

14. A system according to claim 13 wherein the signal processing unit is configured to compare the PPV with one or more PPV magnitude criteria and to determine on the basis of this comparison that the event is not a significant rock fall event.

15. A system according to claim 1 wherein the signal processing unit is configured to ascertain whether the event occurs within a time window $\Delta t_{pre-train}$ of a subsequent train event and if the event does occur within the time window $\Delta t_{pre-train}$ to determine that the event is a train precursor event.

16. A system according to claim 1 wherein the signal processing unit is configured to ascertain whether the event is one of a threshold number (thresh_#) of events that have occurred within a recent time period $\Delta T$ and if the event is one of the threshold number (threh_#) of events that have occurred within the recent time period $\Delta T$ to determine that the event is part of a rock fall accumulation.

17. A system according to claim 1 wherein the signal processing unit is configured to:
    determine a duration $t_{dur}$ associated with the event for the particular one of the ballast sensors based, at least in part, on its corresponding ballast sensor signal and to determine that the event may be a rock fall event if the event duration $t_{dur}$ is less than a duration threshold (thresh_dur); and
    wherein the signal processing unit is further configured, after determining that the event duration $t_{dur}$ indicates that the event may be a rock fall event, to determine a PPV parameter associated with the event for the particular one of the ballast sensors and its corresponding ballast sensor signal, the PPV parameter representing a magnitude of a sample of the corresponding ballast sensor signal with the largest absolute value during the event and to determine that the event is a significant rock fall event when the PPV is greater than the magnitude threshold (thresh_PPV) or a small rock fall event when the PPV is less than the magnitude threshold (thresh_PPV).

18. A system according to claim 17 wherein, prior to determining that the event is a significant rock fall event, the signal processing unit is configured to ascertain whether the event occurs within a time window $\Delta t_{pre-train}$ of a subsequent train event and if the event does occur within the time window $\Delta t_{pre-train}$ to determine that the event is a train precursor event rather than a significant rock fall event.

19. A system according to claim 17 wherein if the signal processing unit determines that the event is a small rock fall event, the signal processing unit is configured to ascertain whether the small rock fall event is one of a threshold number (thresh_#) of small rock fall events that have occurred within a recent time period $\Delta T$ and if the event is one of the threshold number (thresh_#) of small rock fall events that have occurred within the recent time period $\Delta T$ to determine that the event is part of a rock fall accumulation.

20. A system according to claim 1 wherein the signal processing unit detects a plurality of rock fall events associated with a corresponding plurality of ballast sensors based on their corresponding plurality of ballast sensor signals and wherein the signal processing unit is further configured to estimate a location of a rock fall hypocenter based on fitting one or more parameters determined from the corresponding plurality of ballast sensor signals to a model representative of the spatial attenuation of an acoustic signal associated with the rock fall using a curve-fitting optimization technique.

21. A system according to claim 20 wherein the signal processing unit is configured to implement the curve-fitting optimization technique by:
    looping through a plurality of potential hypocenter locations and for each of the plurality of potential hypocenter locations:
        using the one or more parameters determined from the corresponding plurality of ballast sensor signals to determine model parameters that minimize a cost function associated with the model; and
        determining an error metric between one or more parameters predicted by the model and the one or more parameters determined from the corresponding plurality of ballast sensor signals; and
    after completing the loop, selecting a potential hypocenter location with a lowest error metric to be the estimated location of the rock fall hypocenter.

22. A system according to claim 21 wherein the one or more parameters determined from the corresponding plurality of ballast sensor signals comprise, for each ballast sensor signal, a PPV parameter representing a magnitude of a sample of the ballast sensor signal with the largest absolute value during its associated rock fall event.

23. A system according to claim 22 wherein the model comprises at least one of:

$$y(x) = Ae^{-Bx};$$

and $$y(x) = \frac{Ae^{-Bx}}{\sqrt{x}}$$

where: y(x) represents an amplitude of the PPV parameter at a distance x from the rock fall hypocenter, A is a model parameter representative of the PPV at the hypocenter and B is an absorption coefficient model parameter.

24. A system according to claim 23 wherein the signal processing unit is configured to determine whether to trigger an alarm condition based, at least in part, on the model parameter A associated with the lowest error metric and representative of the PPV at the estimated location of the rock fall hypocenter.

25. A system according to claim 1 wherein the signal processing unit detects a plurality of events associated with a particular ballast sensor based on its corresponding ballast sensor signal and wherein the signal processing unit is further configured to determine whether the plurality of events is likely to be a human or other animal in a vicinity of the track section, wherein determining whether the plurality of events is likely to be a human or other animal in the vicinity of the track section comprises determining that a temporal correlation of the plurality of events is greater than a temporal correlation threshold (temp_corr_thresh) and determining that a spatial correlation of the plurality of events is greater than a spatial correlation threshold (spat_corr_thresh).

26. A system according to claim 1 wherein the signal processing unit is configured to determine that the event is a train event or a highrail event by computing a cross-correlation of a pair of ballast sensor signals and comparing the cross-correlation to a magnitude threshold.

27. A system according to claim 26 wherein the signal processing unit is configured to estimate at least one of:
    a speed of the train or highrail vehicle associated with the train event or highrail event; and
    a direction of the train or highrail vehicle associated with the train event or highrail event;
    based at least in part on a time associated with a peak of the cross-correlation.

28. A system according to claim 26 wherein the signal processing unit is configured to compute cross-correlations for a plurality of pairs ballast sensor signals and to estimate an acceleration of the train or highrail vehicle associated with the train event or highrail event based at least in part on the times associated with the peaks of the cross-correlations.

29. A system according to claim 26 wherein the signal processing unit is configured to assign the system one of two states, rock fall or clear-to-pass, and wherein, when the system is in the rock fall state and a train successfully passes the track section, the signal processing unit is configured to change the system state to clear-to-pass.

30. A system according to claim 1 comprising a plurality of rail sensors, each rail sensor operatively contacting the rails or the ties associated with the track section and each rail sensor sensitive to acoustic energy and configured to generate a corresponding rail sensor signal in response to detecting acoustic energy and wherein the signal processing unit is operatively connected to receive the rail sensor signals and is configured to determine that the event is a train event or a highrail event by computing a cross-correlation of a pair of rail sensor signals and comparing the cross-correlation to a magnitude threshold.

31. A system for detection of rock fall in a vicinity of a section of railway track, the system comprising:
a plurality of ballast sensors spaced apart along the track section, each ballast sensor located in a ballast proximate to the track section but spaced apart from rails and ties associated with the track section and each ballast sensor sensitive to acoustic energy and configured to generate a corresponding ballast sensor signal in response to detecting acoustic energy;
a signal processing unit operatively connected to receive the ballast sensor signals from the plurality of ballast sensors, the signal processing unit configured to detect rock fall events in a vicinity of the track section based, at least in part, on the ballast sensor signals;
wherein the signal processing unit is configured to detect a plurality of different types of events comprising rock fall events, train events wherein a train travels over the track section and highrail vehicle events wherein a highrail vehicle travels over the track section and wherein the signal processing unit is configured to discriminate rock fall events from train events or highrail vehicle events;
wherein the signal processing unit is configured to detect an event for a particular one of the ballast sensors based, at least in part, on its corresponding ballast sensor signal;
wherein the signal processing unit is configured to detect a start of the event and an associated time $t_{start}$, for the particular one of the ballast sensors, when an energy parameter associated with the corresponding ballast sensor signal is greater than a start trigger threshold (E_thresh_start), the energy parameter comprising a windowed average of a squared amplitude of the corresponding ballast sensor signal;
wherein the signal processing unit is configured to determine the energy parameter for the corresponding ballast sensor signal according to:

$$E_n = \frac{\sum_{i=n-(d-1)}^{n} (x_i)^2}{d}$$

where: $x_i$ represents a value of an $i^{th}$ sample of the corresponding ballast sensor signal, n is an index of a current sample $x_n$, d is a window duration constant and $E_n$ is the energy parameter.

32. A system according to claim 31 wherein the signal processing unit is configured to detect an end of the event and an associated time $t_{end}$, for the particular one of the ballast sensors, when the energy parameter associated with the corresponding ballast sensor signal is less than an end trigger threshold (E_thresh_end).

33. A method for detection of rock fall in a vicinity of a section of railway track, the method comprising:
providing a plurality of ballast sensors spaced apart along the track section and locating each ballast sensor in a ballast proximate to the track section but spaced apart from rails and ties associated with the track section, each ballast sensor sensitive to acoustic energy and configured to generate a corresponding ballast sensor signal in response to detecting acoustic energy;
receiving, at a signal processing circuit, the ballast sensor signals from the plurality of ballast sensors; and
processing the ballast sensor signals, using the signal processing circuit, to detect rock fall events in a vicinity of the track section based, at least in part, on the ballast sensor signals;
detecting, by the signal processing circuit, a plurality of different types of events comprising rock fall events, train events wherein a train travels over the track section and highrail vehicle events wherein a highrail vehicle travels over the track section and discriminating rock fall events from train events or highrail vehicle events;
detecting, by the signal processing circuit, an event for a particular one of the ballast sensors based, at least in part, on its corresponding ballast sensor signal;
detecting, by the signal processing circuit, a start of the event and an associated time $t_{start}$, for the particular one of the ballast sensors, when a STA/LTA parameter associated with the corresponding ballast sensor signal is greater than a start trigger threshold (thresh_start);
determining, by the signal processing circuit, the STA/LTA parameter for the corresponding ballast sensor signal according to one of:

$$\left(\frac{STA}{LTA}\right)_n = \frac{\frac{\sum_{i=(n-(a-1))}^{i=n} |x_i|}{a}}{\frac{\sum_{i=(n-(b-1))}^{i=n} |x_i|}{b}} \quad (i)$$

where
$b > a > 0$ and $n \geq a, b$ where: $x_i$ represents a value of an $i^{th}$ sample of the corresponding ballast sensor signal, n is an index of a current sample $x_n$, a is an STA duration constant, b is an LTA duration constant and $$\left(\frac{STA}{LTA}\right)_n$$

is the STA/LTA parameter; and $$\left(\frac{STA}{LTA}\right)_{mod,n} = \frac{\sum_{i=(n-(a-1))}^{i=n} x_i}{c} \qquad (ii)$$

where $n > a > 0$ where: $x_i$ represents a value of an $i^{th}$ sample of the corresponding ballast sensor signal, n is an index of a current sample $x_n$, a is an STA duration constant, c is an experimentally determined constant that is representative of an LTA during event free times and $$\left(\frac{STA}{LTA}\right)_{mod,n}$$

is the STA/LTA parameter.

34. A method according to claim 33 comprising detecting, by the signal processing circuit, an end of the event and an associated time $t_{end}$, for the particular one of the ballast sensors, when the STA/LTA parameter associated with the corresponding ballast sensor signal is less than an end trigger threshold (thresh_end).

35. A method according to claim 33 comprising determining, by the signal processing circuit, a duration $t_{dur}$ associated with the event for the particular one of the ballast sensors based, at least in part, on its corresponding ballast sensor signal.

36. A method according to claim 35 comprising comparing, by the signal processing circuit, the event duration $t_{dur}$ to one or more duration criteria and determining, by the signal processing circuit, on the basis of this comparison that the event is not a rock fall event.

37. A method according to 36 comprising determining, by the signal processing circuit, that the event is a train event or a highrail vehicle event when the event duration $t_{dur}$ is greater than the duration threshold (thresh_dur).

38. A method according to claim 37 comprising determining, by the signal processing circuit and for the particular one of the ballast sensors, a PPV parameter which represents a magnitude of a sample of the corresponding ballast sensor signal with the largest absolute value during the event and comparing, by the signal processing circuit, the PPV parameter to one or more magnitude criteria and determining, by the signal processing circuit, on the basis of this comparison whether the event is a train event or a highrail vehicle event.

39. A method according to claim 33 comprising determining, by the signal processing circuit, a spectral power distribution associated with the event for the particular one of the ballast sensors based, at least in part, on its corresponding ballast sensor signal.

40. A method according to claim 39 comprising comparing, by the signal processing circuit, the spectral power distribution with one or more spectral criteria and determining, by the signal processing circuit, on the basis of this comparison that the event is not a rock fall event.

41. A method according to claim 40 wherein the one or more spectral criteria comprise a frequency threshold (thresh_freq) and the method comprises determining, by the signal processing circuit, that the event is a train event or a highrail vehicle event when the spectral power distribution comprises more than the particular percentage of its power at frequencies above the frequency threshold (thresh_freq).

42. A method according to claim 41 comprising determining, by the signal processing circuit and for the particular one of the ballast sensors, a PPV parameter which represents a magnitude of a sample of the corresponding ballast sensor signal with the largest absolute value during the event, comparing, by the signal processing circuit, the PPV parameter to one or more magnitude criteria and determining, by the signal processing circuit, on the basis of this comparison whether the event is a train event or a highrail vehicle event.

43. A method according to claim 33 comprising:
providing one or more rail sensors, each rail sensor operatively contacting the rails or the ties associated with the track section and each rail sensor sensitive to acoustic energy and configured to generate a corresponding rail sensor signal in response to detecting acoustic energy; and
receiving, at the signal processing circuit, the rail sensor signal.

44. A method according to claim 43 comprising determining, by the signal processing circuit, a rail sensor spectral power distribution associated with the event for a particular one of the rail sensors based, at least in part, on its corresponding rail sensor signal and comparing, by the signal processing circuit, the rail sensor spectral power distribution to one or more spectral criteria and determining, by the signal processing circuit, on the basis of this comparison that the event is not a rock fall event.

45. A method according to claim 33 comprising determining, by the signal processing circuit, a PPV parameter associated with the event for the particular one of the ballast sensors and its corresponding ballast sensor signal, the PPV parameter representing a magnitude of a sample of the corresponding ballast sensor signal with the largest absolute value during the event.

46. A method according to claim 45 comprising comparing, by the signal processing circuit, the PPV to one or more magnitude criteria and determining, by the signal processing circuit, on the basis of this comparison that the event is not a significant rock fall event.

47. A method according to claim 33 comprising ascertaining, by the signal processing circuit, whether the event occurs within a time window $\Delta t_{pre-train}$ of a subsequent train event and if the event does occur within the time window $\Delta t_{pre-train}$ determining, by the signal processing circuit, that the event is a train precursor event.

48. A method according to claim 33 comprising ascertaining, by the signal processing circuit, whether the event is one of a threshold number (thresh_#) of events that have occurred within a recent time period $\Delta T$ and if the event is one of the threshold number (threh_#) of events that have occurred within the recent time period $\Delta T$ determining, by the signal processing circuit, that the event is part of a rock fall accumulation.

49. A method according to claim 33 comprising:
determining, by the signal processing circuit, a duration $t_{dur}$ associated with the event for the particular one of the ballast sensors based, at least in part, on its corresponding ballast sensor signal and determining, by the signal processing circuit, that the event may be a rock fall event if the event duration $t_{dur}$ is less than a duration threshold (thresh_dur); and
after determining that the event duration $t_{dur}$ indicates that the event may be a rock fall event, determining, by the signal processing circuit, a PPV parameter associated with the event for the particular one of the ballast sensors and its corresponding ballast sensor signal, the PPV parameter representing a magnitude of a sample of the corresponding ballast sensor signal with the largest absolute value during the event and determining, by the signal processing circuit, that the event is a significant rock fall event when the PPV is greater than the magnitude threshold (thresh_PPV) or a small rock fall event when the PPV is less than the magnitude threshold (thresh_PPV).

50. A method according to claim 49 comprising, prior to determining that the event is a significant rock fall event, ascertaining, by the signal processing circuit, whether the event occurs within a time window $\Delta t_{pre-train}$ of a subsequent train event and if the event does occur within the time window $\Delta t_{pre-train}$ determining, by the signal processing circuit, that the event is a train precursor event rather than a significant rock fall event.

51. A method according to claim 50 comprising, if it is determined that the event is a small rock fall event, ascertaining, by the signal processing circuit, whether the small rock fall event is one of a threshold number (thresh_#) of small rock fall events that have occurred within a recent time period $\Delta T$ and if the event is one of the threshold number (thresh_#) of small rock fall events that have occurred within the recent time period $\Delta T$ determining, by the signal processing circuit, that the event is part of a rock fall accumulation.

52. A method according to claim 33 comprising:
detecting, by the signal processing circuit, a plurality of rock fall events associated with a corresponding plurality of ballast sensors based on their corresponding plurality of ballast sensor signals; and
estimating, by the signal processing circuit, a location of a rock fall hypocenter based on fitting one or more parameters determined from the corresponding plurality of ballast sensor signals to a model representative of spatial attenuation of an acoustic signal associated with the rock fall using a curve-fitting optimization technique.

53. A method according to claim 52 comprising implementing, by the signal processing circuit, the curve-fitting optimization technique by:
looping through a plurality of potential hypocenter locations and for each of the plurality of potential hypocenter locations:
using the one or more parameters determined from the corresponding plurality of ballast sensor signals to determine model parameters that minimize a cost function associated with the model; and
determining an error metric between one or more parameters predicted by the model and the one or more parameters determined from the corresponding plurality of ballast sensor signals; and
after completing the loop, selecting a potential hypocenter location with a lowest error metric to be the estimated location of the rock fall hypocenter.

54. A method according to claim 53 wherein the one or more parameters determined from the corresponding plurality of ballast sensor signals comprise, for each ballast sensor signal, a PPV parameter representing a magnitude of a sample of the ballast sensor signal with the largest absolute value during its associated rock fall event.

55. A method according to claim 54 wherein the model comprises at least one of:

$$y(x) = Ae^{-Bx};$$
and
$$y(x) = \frac{Ae^{-Bx}}{\sqrt{x}}$$

where: $y(x)$ represents an amplitude of the PPV parameter at a distance $x$ from the rock fall hypocenter, $A$ is a model parameter representative of the PPV at the hypocenter and $B$ is an absorption coefficient model parameter.

56. A method according to claim 55 comprising determining, by the signal processing circuit, whether to trigger an alarm condition based, at least in part, on the model parameter $A$ associated with the lowest error metric and representative of the PPV at the estimated location of the rock fall hypocenter.

57. A method according to claim 33 comprising detecting, by the signal processing circuit, a plurality of events associated with a particular ballast sensor based on its corresponding ballast sensor signal and determining, by the signal processing circuit, whether the plurality of events is likely to be a human or other animal in a vicinity of the track section, wherein determining whether the plurality of events is likely to be a human or other animal in the vicinity of the track section comprises determining, by the signal processing circuit, that a temporal correlation of the plurality of events is greater than a temporal correlation threshold (temp_corr_thresh) and determining, by the signal processing circuit, that a spatial correlation of the plurality of events is greater than a spatial correlation threshold (spat_corr_thresh).

58. A method according to claim 33 comprising determining, by the signal processing circuit, that the event is a train event or a highrail event by computing, by the signal processing circuit, a cross-correlation of a pair of ballast sensor signals and comparing, by the signal processing circuit, the cross-correlation to a magnitude threshold.

59. A method according to claim 58 comprising estimating, by the signal processing circuit, at least one of:
a speed of the train or highrail vehicle associated with the train event or highrail event; and
a direction of the train or highrail vehicle associated with the train event or highrail event;
based at least in part on a time associated with a peak of the cross-correlation.

60. A method according to claim 58 comprising computing, by the signal processing circuit, cross-correlations for a plurality of pairs ballast sensor signals and estimating, by the signal processing circuit, an acceleration of the train or highrail vehicle associated with the train event or highrail event based at least in part on the times associated with the peaks of the cross-correlations.

61. A method according to claim 58 comprising assigning, by the signal processing circuit, the system one of two states, rock fall or clear-to-pass, and wherein, when the system is in the rock fall state and a train successfully passes the track section, changing, by the signal processing circuit, the system state to clear-to-pass.

62. A method according to claim 33 comprising:
providing a plurality of rail sensors, each rail sensor operatively contacting the rails or the ties associated with the track section and each rail sensor sensitive to acoustic energy and configured to generate a corresponding rail sensor signal in response to detecting acoustic energy; and receiving the rail sensor signals at the signal processing circuit; and determining, by the signal processing circuit, that the event is a train event or a highrail event by computing, by the signal processing circuit, a cross-correlation of a pair of rail sensor signals and comparing, by the signal processing circuit, the cross-correlation to a magnitude threshold.

63. A method for detection of rock fall in a vicinity of a section of railway track, the method comprising:

providing a plurality of ballast sensors spaced apart along the track section and locating each ballast sensor in a ballast proximate to the track section but spaced apart from rails and ties associated with the track section, each ballast sensor sensitive to acoustic energy and configured to generate a corresponding ballast sensor signal in response to detecting acoustic energy;

receiving, at a signal processing circuit, the ballast sensor signals from the plurality of ballast sensors; and processing the ballast sensor signals, using the signal processing circuit, to detect rock fall events in a vicinity of the track section based, at least in part, on the ballast sensor signals;

detecting, by the signal processing circuit, a plurality of different types of events comprising rock fall events, train events wherein a train travels over the track section and highrail vehicle events wherein a highrail vehicle travels over the track section and discriminating rock fall events from train events or highrail vehicle events;

detecting, by the signal processing circuit, an event for a particular one of the ballast sensors based, at least in part, on its corresponding ballast sensor signal;

detecting, by the signal processing circuit, a start of the event and an associated time $t_{start}$, for the particular one of the ballast sensors, when an energy parameter associated with the corresponding ballast sensor signal is greater than a start trigger threshold (E_thresh_start), the energy parameter comprising a windowed average of a squared amplitude of the corresponding ballast sensor signal;

determining, by the signal processing circuit, the energy parameter for the corresponding ballast sensor signal according to:

$$E_n = \frac{\sum_{i=n-(d-1)}^{n} (x_i)^2}{d}$$

where: $x_i$ represents a value of an $i^{th}$ sample of the corresponding ballast sensor signal, n is an index of a current sample $x_n$, d is a window duration constant and $E_n$ is the energy parameter.

64. A method according to claim 63 comprising detecting, by the signal processing circuit, an end of the event and an associated time $t_{end}$, for the particular one of the ballast sensors, when the energy parameter associated with the corresponding ballast sensor signal is less than an end trigger threshold (E_thresh_end).

* * * * *